United States Patent [19]

Yamauchi

[11] Patent Number: 5,730,124
[45] Date of Patent: Mar. 24, 1998

[54] MEDICAL MEASUREMENT APPARATUS

[75] Inventor: Tadakazu Yamauchi, Saitama, Japan

[73] Assignee: Mochida Pharmaceutical Co., Ltd., Tokyo, Japan

[21] Appl. No.: 505,212

[22] PCT Filed: Dec. 14, 1994

[86] PCT No.: PCT/JP94/02099

§ 371 Date: Aug. 14, 1995

§ 102(e) Date: Aug. 14, 1995

[87] PCT Pub. No.: WO95/16970

PCT Pub. Date: Jun. 22, 1995

[30] Foreign Application Priority Data

Dec. 14, 1993 [JP] Japan .................. 5-313246

[51] Int. Cl.⁶ .................................. A61B 5/00
[52] U.S. Cl. .................................. 128/630
[58] Field of Search .................. 128/630, 632, 128/633, 637, 903, 904, 905, 920, 923; 364/413.01, 413.02

[56] References Cited

U.S. PATENT DOCUMENTS

| | | | |
|---|---|---|---|
| 4,733,354 | 3/1988 | Potter et al. | 128/630 |
| 4,803,625 | 2/1989 | Fu et al. | 364/413.02 |
| 5,023,785 | 6/1991 | Adrion et al. | 128/630 |
| 5,250,419 | 10/1993 | Bernard et al. | 128/635 |
| 5,390,238 | 2/1995 | Kirk et al. | 128/904 |
| 5,437,278 | 8/1995 | Wilk | 128/630 |

FOREIGN PATENT DOCUMENTS

| | | |
|---|---|---|
| A2462466 | 12/1991 | European Pat. Off. . |
| 0525723 | 2/1993 | European Pat. Off. . |
| 2679675 | 1/1993 | France . |
| 61-47565 | 3/1986 | Japan . |
| 61-73058 | 4/1986 | Japan . |
| 61-83944 | 4/1986 | Japan . |
| 63-61157 | 3/1988 | Japan . |
| 63-157040 | 6/1988 | Japan . |
| 4-15035 | 1/1992 | Japan . |
| 4-56561 | 2/1992 | Japan . |
| 4-57161 | 2/1992 | Japan . |
| 4-371134 | 12/1992 | Japan . |
| 4-241028 | 8/1993 | Japan . |
| 5-296851 | 11/1993 | Japan . |
| 5-264552 | 10/1994 | Japan . |

*Primary Examiner*—Jennifer Bahr
*Assistant Examiner*—Bryan K. Yarnell

[57] ABSTRACT

A medical measurement apparatus which includes a measuring unit for outputting electrical signals in the amount of a target analyte measured in a specimen, and a control unit. The control unit has an identification unit for receiving identification data specific to a subject and for identifying that subject on the basis of the identification data; a criterion setting unit only for use by a controller who sets comments and/or commands about measurements regarding the measuring items and the criteria set for the subject and who is capable of making a specialized judgment on the amount of the target analyte in the specimen; and a judgment and display unit and/or judgment and execution unit for computing the measured results based on the electrical signals from the measuring unit and for selectively displaying and/or executing the comments and/or the command relevant to the criteria with respect to the computed measured results.

6 Claims, 19 Drawing Sheets

MEDICAL MEASUREMENT APPARATUS

TECHNICAL FIELD

The present invention relates to a medical measurement apparatus for allowing not only medical experts but also patients, pregnant women and their attendants or helpers to readily perform medical measurement in medical institutions or elsewhere (e.g., at home). More particularly, the invention relates to a medical measurement apparatus which permits health-care or medical experts such as doctors to identify the subject such as a patient or a pregnant woman and to set appropriate comments about that subject with respect to relevant measuring items, to the criteria for judgment and to the measured results, the comments being utilized by the subject depending on the measured results.

The medical measurement apparatus of this invention allows medical measurement to be made by patients or pregnant women themselves as well as by their attendants or helpers. As a matter of convenience, the specification hereunder will refer to the patient, pregnant woman, etc. from whom to collect specimens as "the subject," and the person operating the inventive medical measurement apparatus for measuring the collected specimens as "the operator." The subject and the operator may or may not be the same person.

BACKGROUND ART

A large number of medical measurement systems and apparatuses have been developed for easy use by patients, pregnant women or their attendants carrying out various kinds of medical measurement on their own. The measurements include such items as blood pressure, urine sugar level, urine protein and occult blood, as well as pregnancy tests and observation of mothers' conditions.

Many of the conventional systems and apparatuses utilize test liquids and test paper. In operation, such testing agents require visually inspecting the change in color tone dependent of the amount of the target analyte detected in specimens, whereby the measurements are determined.

Recent years have seen the advent of many other apparatuses that convert an optically measured color tone change into electrical signals or turn the target analyte amount (i.e., concentration) in the specimen into electrical signals. The signals thus obtained are used as the basis for computing measurements that are displayed numerically and/or graphically on a display unit (see Japanese Patents Laid-Open Nos. Sho 61-83944, Sho 63-61157, etc.).

Some medical measurement systems performing electrical measurement store measured results in the past on a number of occasions and allow them to be retrieved later and displayed as needed to make more accurate medical measurements and diagnosis. Other systems comprise a mechanism that generates an alarm if the measuring conditions such as temperature and the target analyte concentration in the specimen are not appropriate (see Japanese Patents Laid-Open Nos. Sho 63-157040, Sho 61-47565, etc.).

Japanese Patent Laid-Open No. Hei 5-296851 discloses a body temperature data management system comprising a clinical thermometer equipped with an LED. When the LED on the clinical thermometer blinks to generate digital signals representing body temperature measurements of the subject on a time series basis, the system properly reads the optical signals to have the body temperature data transferred thereto in a cord-free environment. The body temperature data is stored along with ID information on the subject and the time stamps of the measurement, to be displayed later graphically or otherwise on a display unit.

The majority of the conventional medical measurement systems and apparatuses have their measuring items fixedly determined beforehand, and numerically display such diverse measurements as urine sugar level and blood pressure. The judgment on the measured results is entrusted to the operator (i.e., subject) who may have no specialized knowledge of the field in question.

Some systems have the ability to judge and indicate that a particular measurement is excessively high or low (too large, too small, etc.) relative to the relevant standard range (see Japanese Patent Laid-Open No. Sho 61-73058). However, such judgments are set generally for all subjects; judgments tailored to individual subjects cannot be performed.

If the medical measurement systems with a measurement storage feature measure irrelevant subjects or perform measurement under faulty ambient conditions, such measurements are still stored unchecked. When viewed later by doctors and other experts, totally irrelevant measurements can be taken as valid clinical data, which can result in misdiagnosis.

The above-cited body temperature data management system disclosed in Japanese Patent Laid-Open No. Hei 5-296851 has the function of managing body temperature data based on the ID information about specific subjects. This system, too, simply measures body temperatures and stores the measurements in a fixed manner. The system has no capability for making appropriate and fine-tuned judgments tailored to individual subjects on the basis of their body temperature data.

In recent years, various forms of remotely provided medical care (generally called home care) have been on the rise. In particular, patients with chronic diseases or in the chronic stage of their disorders are often taken care of at home and not in the hospital, with a view to improving the quality of life for the patients. For example, patients who are bedridden due to cerebral disorders or because of their advanced ages, patients with chronic nephritis, diabetes, cancer, coronary and hepatic disorders, infertile women, and pregnant women are fit to receive home care. These home-care or self-managing patients live outside medical institutions and thus require more adequate and rigorous supervision by doctors and other experts than in-patients. The home-care patients are apt to become anxious about their conditions, and the doctors and experts in charge of these patients are required to spend much more time on them than on in-patients in terms of remotely conducted examination and consultations by telephone. Because of the current constraints on the number of doctors and experts and on the facilities available for home care, there is an urgent need for medical care management technology for caring individual patients efficiently, appropriately and in an individually customized manner.

The conventional techniques are capable of managing a large number of patients in a fixed manner, but are incapable of establishing or modifying the measuring conditions, the criteria for judgment, or corresponding remedies and treatments for individual patients. Because important judgments are left for the patient to make, it is difficult for the experts managing the system to deal with sudden changes in the patient's conditions quickly and adequately. Although there exist means of communication and data transfer systems which the doctors or experts may use to manage and transfer the measured data on patients in remote locations, the fact remains that the doctors or experts in charge must keep constant surveillance over the data on numerous patients.

Despite the dedicated facilities and human resources, the patients are unable to feel reassured that they are adequately taken care of based on their measured results. The means and systems for communicating and transferring measured data between remote locations are apparently effective in reducing the number of times each patient visits the hospital or the number of times the patient is personally examined by the doctor. However, what these facilities can do is simply to replace the hospital visits or the examinations in hospital with transfers of data or judgments on those data remotely made. There have yet to be solutions to the problems of how to reassure both the patient and the doctor about the effectiveness of home care while alleviating the burdens on both of them in a home-care environment.

One solution to such problems is a home care support system that connects patients' terminals with a central control unit via means of communication (as disclosed in Japanese Patent Laid-Open No. Hei 4-15035). This system, dependent on computer-based communications, requires its central control unit to judge information input through the patients' terminals (ID inquiry, measured data, answers to questions) and to transmit the judged results to the terminals. If the means of communication becomes faulty or unavailable, measuring operations may not be carried out or the judged results may not be transmitted. This can cause serious medical problems to patients who must take emergency measurements or who need continuous testing. Furthermore, the system does not allow the doctor to manage individual patients on the basis of time information (i.e., time stamps of measurements) or of the measuring items. Because unnecessary or irrelevant measurements cannot be excluded, the system is incapable of administering home care effectively.

DISCLOSURE OF THE INVENTION

It is therefore an object of the present invention to overcome the above and other deficiencies and disadvantages of the prior art and to provide a medical measurement apparatus allowing the subject such as patients and pregnant women or their attendants to conduct various kinds of medical measurement at home or elsewhere outside medical institutions. With the subject identified and with the individual's symptoms, physical conditions, constitution and environment verified, a doctor or a medical expert with specialized knowledge sets to the apparatus the measuring items, the criteria for judgment, and comments and/or commands corresponding to the measured results. Given the criteria and other relevant items, the apparatus outputs judgments on the measured results, and issues appropriate comments and executes commands in keeping with such judgments. The subject can then make effective use of such comments and the result of command execution in accordance with the measured results.

In achieving the foregoing and other objects of the present invention and according to one aspect thereof, there is provided a medical measurement apparatus comprising a measuring unit for outputting electrical signals in accordance with the amount of a target analyte measured in a specimen, and a control unit. The control unit includes: identification means for receiving identification data specific to a subject and for identifying that subject on the basis of the identification data; criterion setting means only for use by a controller who sets comments about measured results regarding the measuring items and the criteria set for the subject and who is capable of making a specialized judgment on the amount of the target analyte in the specimen; and judgment and display means for computing the measurements based on the electrical signals from the measuring unit and for selectively displaying the comment relevant to the criteria with respect to the computed measured results.

In a preferred embodiment of the invention, the identification data is set only by the controller. In another preferred embodiment of the invention, the control unit includes storage means for storing a plurality of measurements, and the controller retrieves the stored measurements as desired.

In a further preferred embodiment according to the invention, the control unit is constituted so that the measurements are stored in said storage means, and said criteria can be modified in accordance with said stored measurements.

In an even further preferred embodiment of the invention, the control unit includes either or both of questioning means and verification means, the questioning means being used to put preliminary questions to the subject in connection with the measuring items, the verification means being utilized to verify that measurement is performed under the measuring conditions established in accordance with the measuring items, and only the controller is allowed to set the preliminary questions and the measuring conditions.

In a still further preferred embodiment of the invention, the control unit includes time stamp setting means for setting timer-counted time stamps to be measured in keeping with the measuring items, and time stamp verification means for verifying that a given measurement was taken at the correspondingly set time of day, and only the controller is allowed to set the time stamps.

In a yet further preferred embodiment of the invention, the criterion setting means in the control unit is arranged to set commands either in place of or in conjunction with the comments, and the judgment and display means is either replaced with or supplemented by judgment execution means for selectively executing the commands.

BEST MODE FOR CARRYING OUT THE INVENTION

The preferred embodiment of the invention will now be described with reference to the accompanying drawings.

Figure 1:
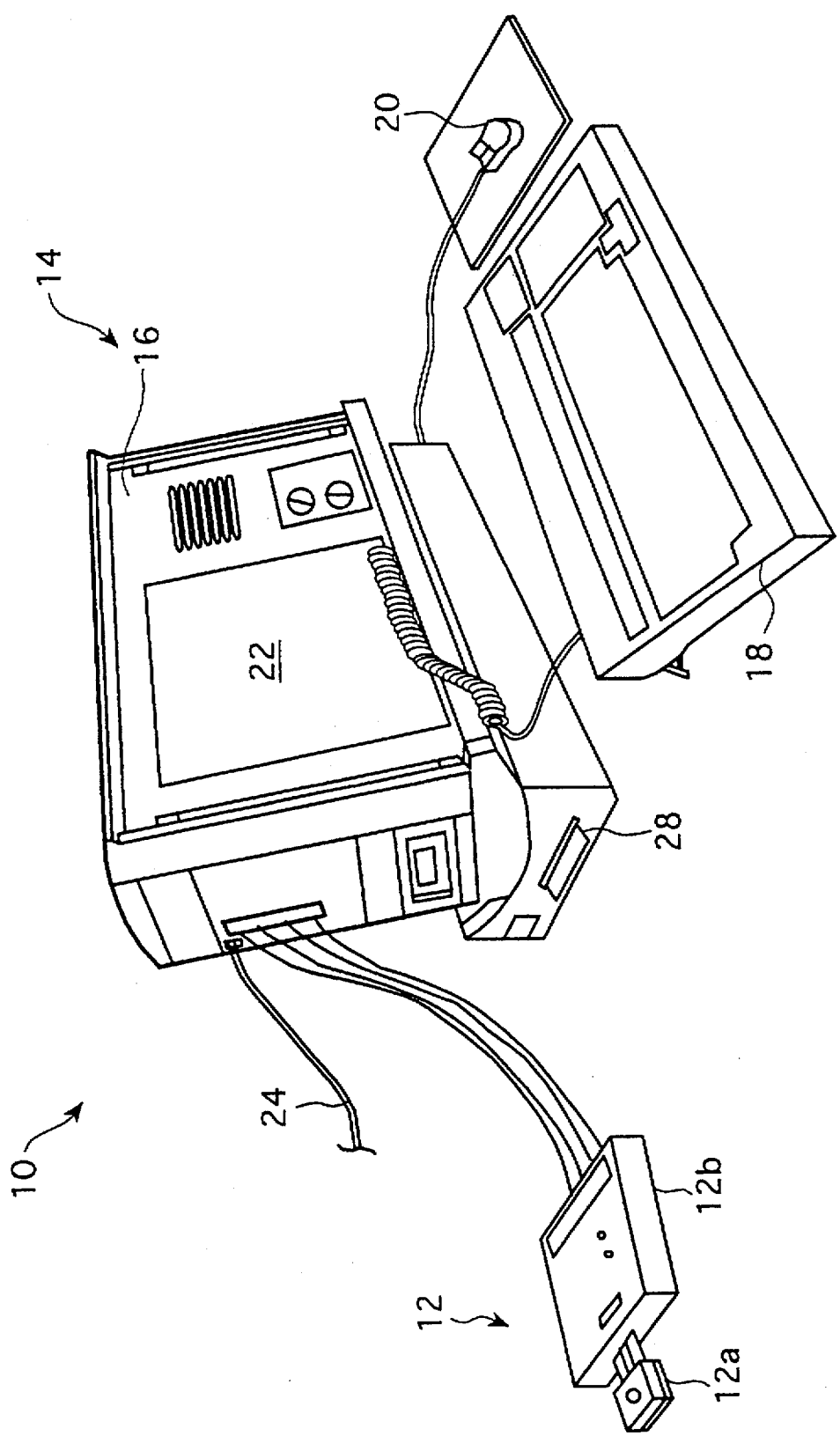
FIG. 1 is a conceptual view of an example of the medical measurement apparatus practiced as the preferred embodiment of the invention.

FIG. 1 is a conceptual view of a medical measurement apparatus practiced as the preferred embodiment of the invention.

The medical measurement apparatus 10 in FIG. 1 is one which allows not only health-care professionals such as doctors and nurses but also the subject such as patients, pregnant women and their attendants to readily perform medical measurement (testing) in medical institutions or elsewhere (e.g., at home). As illustrated, the medical measurement apparatus 10 primarily comprises a measuring unit 12 and a control unit 14 that receives data from the measuring unit 12 so as to output and display measurements. The control unit 14 includes a control unit body 16, and input means such as a keyboard 18 and a mouse 20 used to input various conditions and the subject's ID data to the system. The control unit body 16 is equipped with a display unit 22 that displays measured results and various comments.

The control unit 14 further comprises a drive unit 28 that writes and reads data to and from a storage medium for preserving measured results and personal information. The storage medium may be a floppy disc, a hard disc, an optical disc, a magneto-optical disc, an IC card, an IC memory card, an optical card or a magnetic card. The control unit 14 has a communication line 24 connected as needed to a host computer or a server at the controller's site in medical institutions. The drive unit 28 may be incorporated in, or attached externally to (or auxiliary), the control unit 14.

The input device of the invention may be something other than the keyboard 18 or mouse 20 illustrated; it may be a push button arrangement, a pen input device, a touch panel or a voice input unit. The input device may utilize a storage medium such as a magnetic card, an IC card, an optical card, an IC memory card or a floppy disc. All known input devices may be usable with the invention. The display unit 22 may be an LCD, a CRT unit or a voice output unit, or it may be a hard copy output device such as a printer. The display on the screen may include not only characters but also pictures including animation.

A plurality of input and display devices may be provided in suitable combination. For example, operating instructions, entry prompts and/or experts' comments may be displayed in characters and pictures or may be output as a voice. Such arrangements will make the operation of the apparatus easier and subject to fewer errors. When comments are printed out in hard copy, they can be preserved for later use by the operator.

The measuring unit 12 has a section for taking measurements of the subject's specific parts, a section for receiving a specimen collected from the subject, or a section for accommodating test paper or a sample holder containing the specimen. With measurements taken, the measuring unit 12 outputs electrical signals representative of the subject's measuring item or of the amount of the target analyte in the specimen. In FIG. 1, the measuring unit 12 is composed of an analyzing section 12a such as a sensor chip and of an output section for converting the output from the analyzing section 12a into electrical signals for output to the control unit 14. The analyzing section 12a may be either incorporated beforehand in the output section 12b, or may be attached (i.e., loaded) to the output section 12b at the time of measurement. The medical measurement apparatus 10 of the invention is not limited in terms of the way in which the measuring unit 12 (analyzing section 12a) generates (outputs) signals representing the amount of the target analyte in the specimen, i.e., in the way the target analyte amount is measured. Any known specific analysis methods may be utilized. Preferably, the measuring unit 12 should make use of immunoassay, nucleic acid assay, ligand-receptor assay or the like. The most preferred method of analysis is immunoassay.

Specific reactions of the target analyte under test may be obtained and reaction-caused changes may be detected with the apparatus 10. In such cases, a conductivity meter is used if changes are caused in conductivity by reaction; a potentiometer is used if potential differences are brought about by reaction; a potentiostat, a coulomb meter, an ammeter or other appropriate electrical measuring device is used if the reaction involved is an electrochemical reaction; a fluorometer is used if the reaction entails fluorescence; a luminometer is used if the reaction is accompanied by luminescence; and a color-difference meter, a photometer or a reflectometer is used if the reaction involves coloration. Preferably, the electrical measuring device should be employed.

Figure 2:
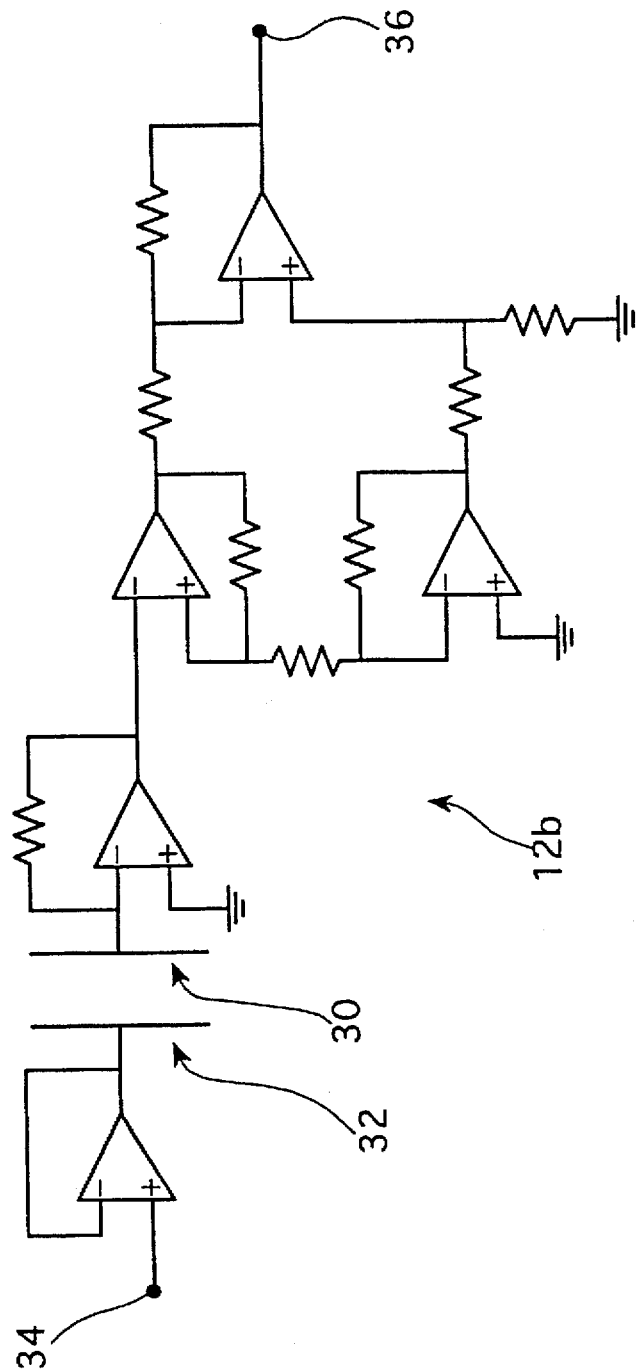
FIG. 2 is an example of the circuit diagram of the output section in the measuring unit of the embodiment in FIG. 1.

FIG. 2 is a circuit diagram of the output section 12b in the measuring unit 12 of the embodiment, the output section 12b generating electrical signals representing the amount of the target analyte detected in the subject's specimen through electrochemical reaction. A WE terminal 30 and a CE terminal 32 are connected respectively to a working electrode and a counter electrode terminal of the analyzing section 12a. A D/A terminal 34 and an A/D terminal 36 are connected respectively to a digital-analog (D/A) conversion circuit terminal and an analog-digital (A/D) conversion circuit terminal of the control unit 14. With this embodiment, the D/A and A/D conversion circuits are located in a multi-function data I/O board AT-MIO-16X (from National Instruments) housed in the control unit body 16. The example of FIG. 2 constitutes a potentiostat circuit. The potential output by the control unit 14 via the D/A terminal 34 is applied between the working electrode and counter electrode terminals of the analyzing section 12a. A current flows through the working electrode terminal of the analyzing section 12a in response to the amount of the target analyte in the specimen. The detected current is converted to a potential by a current-potential conversion circuit, and the potential is amplified by an amplifier circuit to form electrical signals that are sent to the control unit 14 via the A/D terminal 36.

The control unit 14 computes values form the received electrical signals. The computed values are compared with criteria that have been set beforehand by the controller for the subject in question. The control unit 14 then outputs a controller-predetermined judgment on the measured results, or output comments or executes commands in keeping with the judgment.

The analyzing section 12a that generates electrical signals representing the amount of the target analyte in the subject's specimen through electrochemical reaction may be any One of diverse sensors including an enzyme sensor, an immunosensor, a nucleic acid sensor, a microorganism sensor, a biosensor, a chemical sensor, a semiconductor sensor and a gas sensor (A. P. F. Turner, I. Karube and G. S. Wilson, Biosensors—Fundamentals and Applications, 1987; Electrochemical Sensors in Immunological Analysis, 1987; E. A. H. Hall, Biosensors, 1990).

Below is a description of an analyzing section adopting an electrochemical enzyme immunoassay technique known as MEDIA (mediator diffusion-controlled immunoassay), as disclosed in Japanese Patent Laid-Open No. Hei 5-264552.

Figure 3:
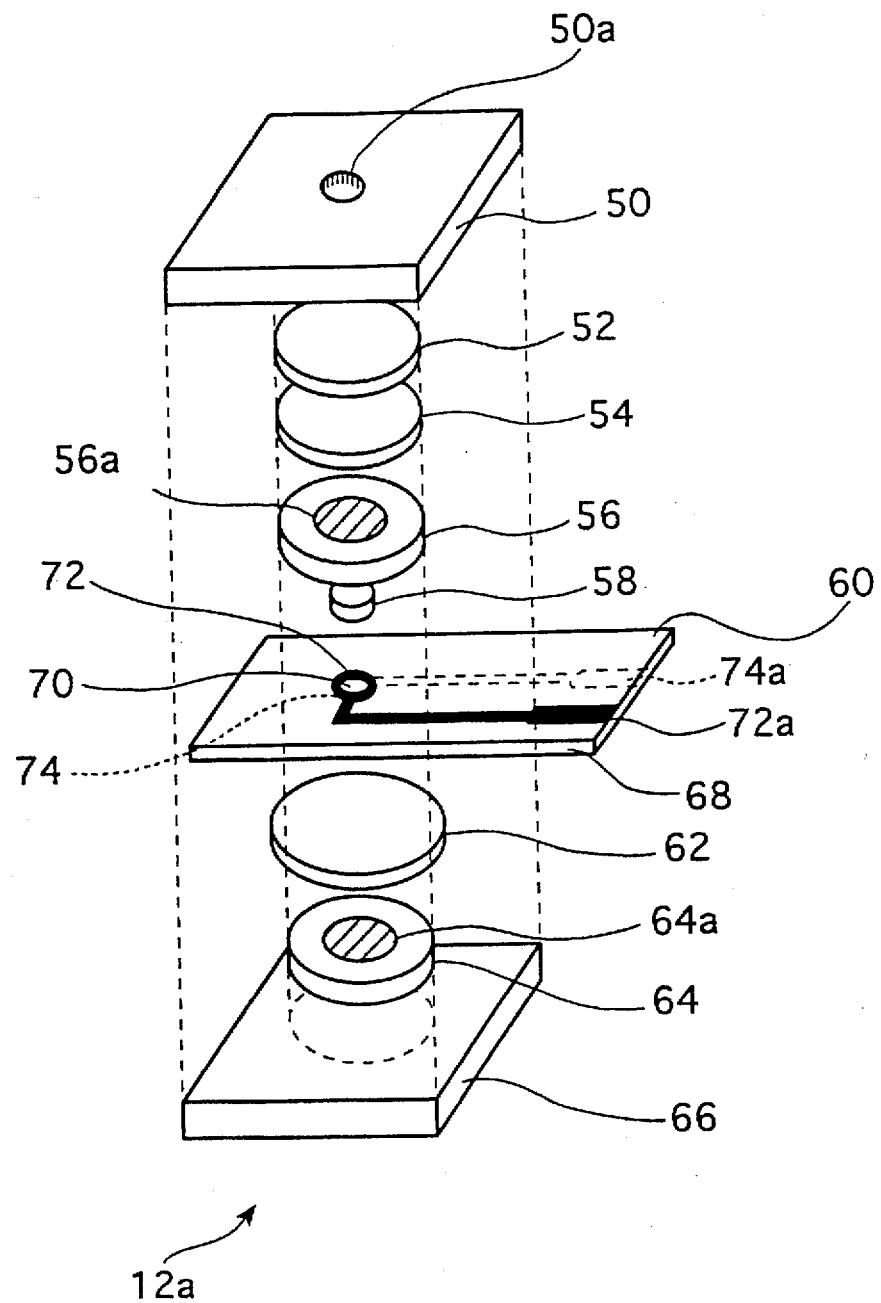
FIG. 3 is a schematic exploded perspective view of an example of the analyzing section in the measuring unit of the embodiment in FIG. 1.
Figure 4:
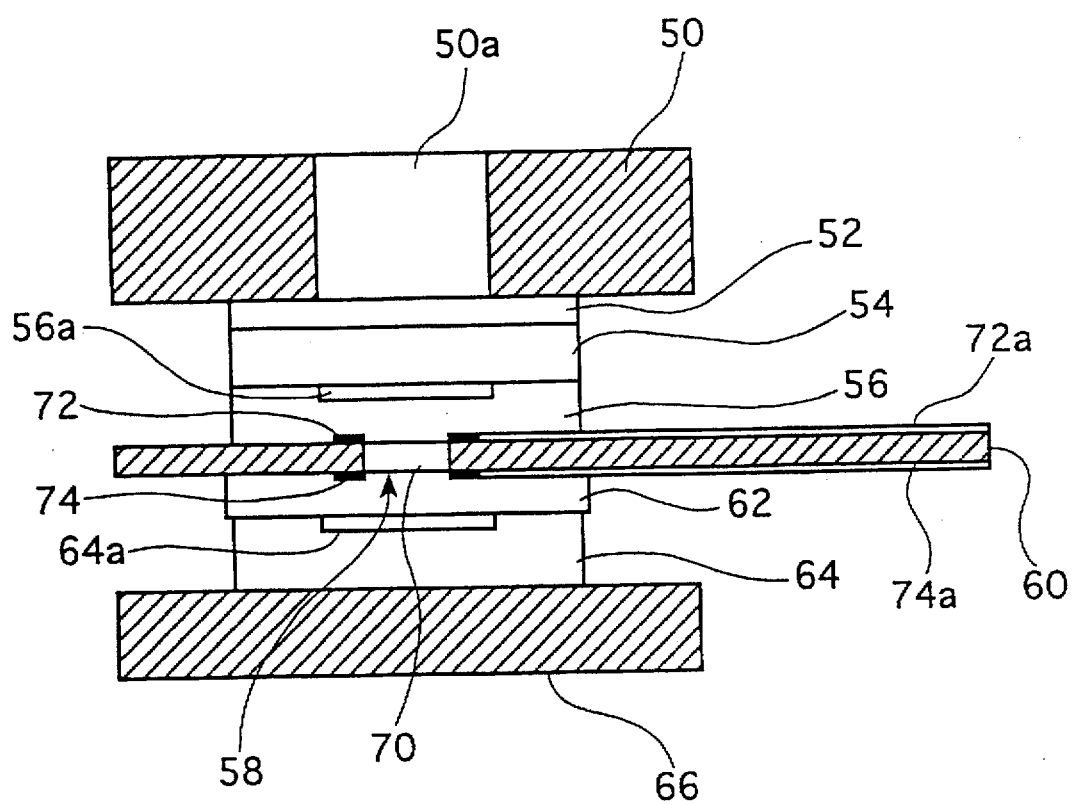
FIG. 4 is a cross-sectional view of the analyzing section in FIG. 3 as it is assembled.

FIGS. 3 and 4 are schematic views of such an analyzing section 12a.

This type of analyzing section 12a employs urine as specimen liquid to assay the quantity of urine hCG (human chorionic gonadotropin). The result of the assay is used for diagnosis of pregnancy.

The analyzing section 12a has an acrylic lower plate 66 supporting an absorber 64 in the form of a round cellulose filter paper (12 mm diameter) impregnated with a mixture of hydrogen peroxide and urea and freeze-dried. As illustrated, the absorber 64 has a sealing portion 64a on the upper side surface of the absorber 64 (this side will be regarded as the face and the other side as the back). The sealing portion 64a of a round, liquid-impermeable seal (6 mm diameter) is pasted on the central portion of the upper side surface of the absorber 64.

Above the absorber 64 is a stack of round, porous, anti-hCG antibody-insolubilized membrane 62 (13 mm diameter).

An electrode plate 60 is placed on top of the antibody-insolubilized membrane 62. The electrode plate 60 is made of a PET film (18×44 mm). The face and the back of the PET film have a ring-like silver electrode (6 mm in outer diameter, 3 mm in inner diameter) and a ring-like carbon electrode (6 mm in outer diameter, 3 mm in inner diameter) screen-printed respectively thereon, the two electrodes being axially aligned. Thus the electrode plate 60 has the ring-like shaped silver printed electrode (counter electrode 72) on its face and the ring-like shaped carbon printed electrode (working electrode 74) on its back. A Counter electrode terminal 72a and a working electrode terminal 74a are connected respectively to the counter electrode 72 and the working electrode 74. Conductors other than the ring-like shaped electrodes (72 and 74) and the terminals (72a and 74a) are covered with resist ink and are not exposed. The electrode plate 60 also has a through hole 70 (3 mm diameter) that penetrates the center of the two electrodes. The electrode plate 60 is mounted so that the through hole 70 is aligned axially with the antibody-insolubilized membrane 62. The through hole 70 is fitted with a connecting part 58 made of a round, glass fiber filter paper (3 mm diameter).

On top of the electrode plate 60 is placed a round, glass fiber filter paper 56 (12 mm diameter) treated by surface active agent. The filter paper 56 is axially aligned with the through hole 70. A round, liquid-impermeable seal (6 mm diameter) is pasted as a sealing part 56a onto the center portion of the surface of the glass fiber filter paper 56.

Over the glass fiber filter paper 56 is an enzyme labeled antibody-impregnated part 54 axially aligned with the filter paper 56 below. The enzyme labeled antibody-impregnated part 54 has peroxidase enzyme labeled anti-hCG antibody solution impregnated in a round glass fiber filter paper (12 mm diameter) and freeze-dried therein. A round, nonwoven fabric portion (12 mm diameter) is further placed as a filter part 52 onto the enzyme labeled antibody-impregnated part 54.

The analyzing section 12a is topped with an acrylic upper plate 50 having a specimen inlet port 50a (6 mm diameter). The specimen inlet port 50a of the upper plate 50 is axially aligned with the filter part 52 below. The analyzing section 12a is assembled by screwing the upper plate 50 to the lower plate 66.

For analysis, the working electrode terminal 74a conducting to the working electrode 74 of the analyzing section 12a is connected to the WE terminal 30 of the output section 12b; the counter electrode terminal 72a conducting to the counter electrode 72 is connected to the CE terminal 32 of the output section 12b. Alternatively, the analyzing section 12a and output section 12b may be integrated so that the working electrode terminal 74a and the counter electrode terminal 72a double respectively as the WE terminal 30 and the CE terminal 32.

The operator introduces a urine specimen together with an electron mediator compound such as p-benzoquinone into the specimen inlet port 50a of the analyzing section 12a. Measurement is started by the operator pushing a measurement start button on the control unit 14, to be described later.

With measurement started, the control unit 14 causes the output section 12b to apply a potential of −200 mV between the working electrode 74 (terminal 74a) and the counter electrode 72 (terminal 72a) of the analyzing section 12a, and measures the reduction current through the working electrode 74 every second. Current measurements taken over three to five minutes following the start of measurement are averaged. The average is put into standardized relational functions incorporated in advance into the arithmetic processing mechanism in the control unit 14, whereby the hCG concentration in the specimen is computed. The computed value is compared with the criteria established by the controller in the control unit 14.

The liquid specimen introduced into the analyzing section 12a in the manner described passes through the filter part 52 that removes aggregates and other impurities from the liquid. The specimen liquid then dissolves the enzyme labeled antibody of the enzyme labeled antibody-impregnated part 54, bypasses the sealing part 56a and flows into the glass fiber filter paper 56. During that time, the hCG antigen in the specimen liquid is bound with the enzyme labeled antibody to form an antigen-enzyme labeled antibody complex. The liquid specimen further passes through the connecting part 58 and the through hole 70 of the electrode plate 60 to enter the antibody insolubilized membranes 62, bypassing the sealing portion 64a below. The liquid penetrates through the antibody insolubilized membranes 62 radially from the center to the periphery, to be absorbed into the absorber 64 to dissolve a sufficient amount of enzyme substrate therein.

While the specimen liquid is penetrating through the antibody insolubilized membrane 62 radially, the antigen-enzyme labeled antibody complex mentioned above is further bound with an insolubilized antibody to form a sandwich type complex (insolubilized antibody-antigen-labeled antibody complex). For this to take place, the antibody insolubilized membrane 62 have a distribution of the labeling enzyme formed in accordance with the amount of the antigen by the sandwich-type binding to the labeled antibody and the insolubilized antibody. That is, the greater the amount of the antigen in the specimen liquid, the more localized the labeled enzyme toward the center of the round antibody insolubilized membrane 62. Conversely, the smaller the amount of the antigen in the specimen liquid, the more dispersed the labeling enzyme throughout the antibody insolubilized membrane 62.

In the analyzing section 12a utilizing the MEDIA method, the electron mediator mediates between the ring-like shaped working electrode 74 contacting the center portion of the antibody insolubilized membranes 62 on the one hand, and the labeling enzyme distributed in the antibody insolubilized membrane 62 on the other hand. Through mediation of the electron mediator, the oxidation reduction reaction of the labeling enzyme is measured as a current. In the example above, p-benzoquinone (i.e., electron mediator) mediates recyclically between the reaction of peroxidase (labeling enzyme) with the hydrogen peroxide substrate on the one hand, and the electrode reaction of the working electrode 74 on the other. In this setup, the reduction current of the electron mediator caused by the electrode reaction at the working electrode 74 is measured. The reduction current whose intensity depends on the mass transfer through diffusion of the electron mediator is significantly affected by the distance distribution between the labeling enzyme molecules and the working electrode 74. Thus the larger the number of labeling enzyme molecules localized toward the center of the antibody insolubilized membranes 62 due to a high amount of the antigen in the specimen, the larger the current. Conversely, the more dispersed the labeling enzyme molecules throughout the antibody insolubilized membranes 62 due to a low amount of the antigen in the specimen, the smaller the current. It follows that with standardized relational functions obtained by prior analysis of specimens containing the antigen of standard concentration, the concentration of the antigen in the specimen in question is computed from the current value in the form of electrical signals.

Described above is the example in which the measuring unit 12 made of the analyzing section 12a and output section 12b utilizes electrochemical reaction. Alternatively, any other method or device for generating electrical signals reflecting the amount of the target analyte in the specimen may be used as the measuring unit 12 of the medical measurement apparatus embodying the invention.

The signals from the measuring unit 12 (i.e., measurements obtained by the measuring unit 12) are sent to the control unit 14.

As illustrated, the control unit 14 comprises the control unit body 16 having the display unit 22, the keyboard 18, and the mouse 20 that may be attached as needed. Given the signals from the measuring unit 12, the control unit 14 computes the measured results and displays the measured results on the display unit 22 along with relevant comments. The control unit 14 may also execute commands in accordance with the acquired measurements. The control unit body 16 is a processing unit incorporating a microprocessor. The processing unit should preferably be a computer or the like in view of versatility and expandability. This embodiment utilizes the lap-top computer Portable 486c (from Compaq) that is partially expanded. The above-described measuring unit may be either incorporated in the control unit body 16 or attached thereto externally.

The control unit 14 is not limited to a computer. It may be any device which permits the use of a processing unit, a storage unit, a display unit and an input unit and which connects to or incorporates a measuring unit. Another alternative is to integrate the control unit and the measuring unit.

A major application of the inventive medical measurement apparatus is found in the situation of remotely provided medical care such as a home-care setup. Typical configurations of the apparatus for remotely provided medical care will now be described.

Where the control unit 14 of the measuring unit 12 is made portable, the controller such as a doctor stores the criteria for judgment and the comments or commands about the acquired measured results with respect to the criteria into the storage device of the control unit 14, and hands the control unit 14 over to the operator. The storage device in the control unit 14 may be any one of a backed-up RAM, a hard disc, a magneto-optical disc, a floppy disc, an IC card, an IC memory card, an optical card and a magnetic card. The operator carries the control unit 14 home or somewhere outside for measurement, takes measurements on the spot, and acts on the results using the criteria and comments or commands established by the controller. When paying a visit to the controller, the operator carries with him the control unit 14. The controller then retrieves the measurements from the storage device for reference. Such stored measurements may be used not only as information by which the operator or the subject has a better understanding of his pathologic condition, but also as information according to which the controller diagnoses the subject. Depending on the circumstances or condition of the subject, the controller may modify the criteria or the comments or commands regarding the measurements with respect to the criteria, store the modifications in the storage device of the control unit 14, and hand the control unit 14 back to the operator.

Even where the control unit 14 is not arranged to be portable, the controller such as a doctor may modify the criteria or the comments or commands regarding the measurements with respect to the criteria, store the modifications into a portable storage device of the control unit 14 via the host computer or server, and hand the portable storage device back to the operator. The portable storage device may be any one of an IC card, an IC memory card, an optical card, a magnetic card, a floppy disc, a hard disc card, an optical disc and a magneto-optical disc (MO). For measurement, the operator connects the storage device to the control unit 14 located at home or somewhere outside, takes measurements on the spot, and acts on the results wherever he is by use of the criteria and comments or commands established by the controller. The measured results are stored into the storage device. When paying a visit to the controller, the operator carries the storage device with him. The controller then retrieves the measurements from the storage device for reference using the control unit body as the host computer. Depending on the circumstances or condition of the subject, the controller may modify the criteria or the comments or commands regarding the measured results with respect to the criteria, store the modifications into the storage device, and hand the storage device back to the operator.

In the above configurations of the apparatus, fine-tuned diagnostic settings are available for individual subjects. In that case, both the controller and the subject feel reassured that the subject is being properly cared for under the controller's supervision. It is then possible for the measured results to be judged quickly according to the controller-established criteria so that relevant comments or commands prompt the operator or the subject to take appropriate action or to suppress unnecessary behavior. As a result, the burdens on the controller, the operator and the subject are all alleviated.

Another application of this apparatus is a configuration comprising communication lines or networks. In this case, the control unit 14 is composed of a control unit body acting as the host computer or server, and of one or a plurality of terminals or clients each including a measuring unit 12. This system configuration connects the host computer or server on the controller's side with the subject's terminal or client using a communication line 24 or the like. The controller may then take note of the subject's pathologic condition in real time, issue appropriate instructions and/or take relevant action accordingly.

In a relatively restricted area such as inside the hospital, a LAN setup illustratively based on the Ethernet may be used for communication purposes. Where remote locations are involved, a leased line network or a public network may be employed. The communication line may be either a physical line such as a telephone line or wireless circuits such as those utilizing a communication satellite.

Figure 5:
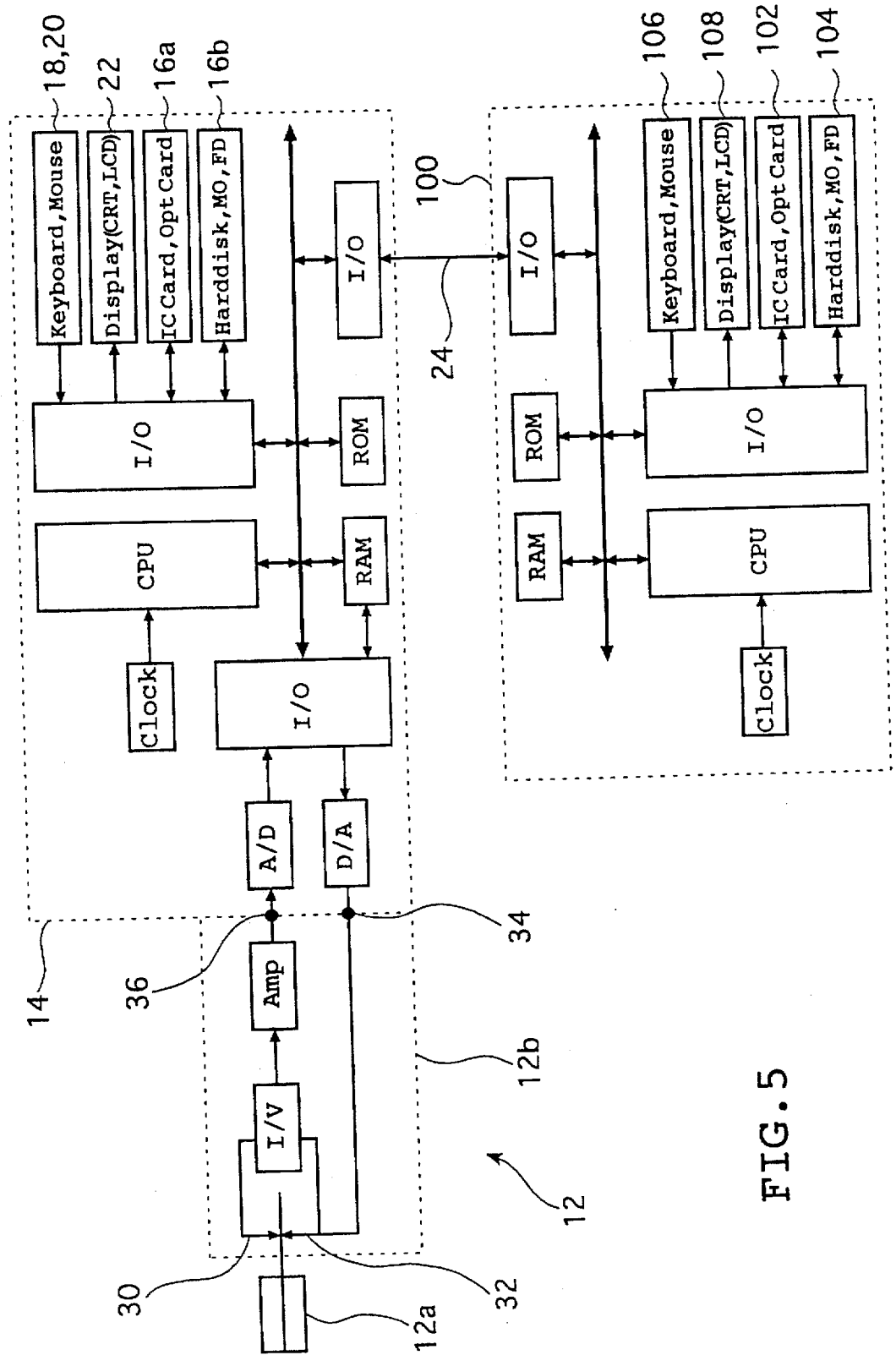
FIG. 5 is a schematic view showing an example of typical signal connections between the measuring unit and the control unit of the embodiment.

FIG. 5 is a schematic view showing typical signal connections between the measuring unit 12, the control unit 14 and a host computer or server 100. The storage device of the control unit 14 or that of both the control unit 14 and the host computer or server 100 accommodates a group of control commands for controlling the measuring unit 12 during measurement, the criteria for judgment established by the controller, and comments and commands about the measured results with respect to the criteria. The storage device may be any one of a ROM, a backed-up RAM, a card medium 16a and 102 such as an IC card, an IC memory card, an optical card and a magnetic card; and a storage medium 16b and 104 such as a hard disc, a magneto-optical disc, a floppy disc, a magnetic tape and a DAT. In FIG. 5, reference numeral 106 indicates an input device such a mouse and a keyboard of the host computer or server 100, and reference numeral 108 is a display unit of the host computer or server 100.

Below is an example in which the controller establishes various diagnostic settings using the host computer or server 100, with a remotely located operator using the control unit 14 for measurement and medical care via the communication line 24.

For this example, it is assumed that at least the control unit 14 stores a group of control commands for controlling the control unit 14.

When the operator starts the control unit 14, a group of control commands is retrieved from the storage device of the control unit 14 to control the control unit 14. With measurement completed, the measured results are written to the storage device of the controller's host computer or server 100 and/or to the storage device of the control unit 14. Where necessary, the controller may retrieve for reference the measurements from the storage device of the host computer or server 100. On the basis of the measured results, the controller may operate the host computer or server 100 to modify as needed the criteria for judgment as well as the comments and/or commands about the measurements with respect to the criteria. The above scheme allows the control unit 14 to make measurement even if the communication line becomes faulty. Thus the scheme is safe and preferable.

The measured results may be stored in one or both of the two storage devices: one for the control unit 14 on the operator's side, the other for the host computer or server 100 on the controller's side. The measured results may include computed values regarding the target analyte in the specimen, the operator's name, the operator code, the subject's name, the subject code, dates of measurements, time stamps of measurements, and the operator's answers to preliminary questions. Where storage addresses and storing methods are standardized, the subject or operator may receive individual supervision concurrently from a plurality of controllers. If the measured results are written to the storage device of the control unit 14, the subject or the operator can readily reference his past measurements therefrom. This is preferable in terms of better self-care. In particular, the storage device is preferably detachable, such as the card medium 16a (e.g., IC card), floppy disc or the like. Such storage devices will allow the subject or the operator to utilize advantageously a plurality of control units 14 (at home, in the office, etc.). Because the subject or the operator can readily handle the portable card or like medium on his own, the subject or the operator finds it easy to manage his own medical data. This aspect of individual data management is desirable in view of protection of privacy. Furthermore, the easy handling of the storage medium makes it easier for a plurality of subjects and operators to share a single control unit 14.

On the other hand, if the measured results are written to the storage device attached to the host computer or server 100, the controller such as a doctor may build the pathologic conditions of a plurality of subjects (e.g., patients) illustratively into a database for collective supervision, which is desirable for better health care from the controller's viewpoint. For this to be implemented, the measurements may be written both to the storage device of the control unit 14 and to the storage device of the host computer 100. For efficient communication, the measured results may preferably be transferred in batch form to the host computer or server when data transfer is requested by the controller, when the measured results have reached a threshold level (to trigger a command), or when the storage device of the control unit has become full. Under certain circumstances, it is also preferable to trigger data transfer depending on the answer to a preliminary question. Any or all of the above alternatives may be selected in consideration of the pathologic conditions of the subject to be supervised, the life styles of the controller and of the subject, and the costs involved (communication costs in particular). If the communication path fails, rendering the communication unavailable, the settings and the measurements are still held in the storage device of the control unit In that case, there is no problem with measurement and judgment on the part of the control unit 14.

The above-mentioned connection based on the communication line can afford additional benefits to the medical measurement apparatus of the invention. For example, in a home-care situation, it is important to respect the patient's right to know. In particular, a self-managing patient should preferably be encouraged to take ac active part in the performance of medical care so as to gain better therapeutic results. With this apparatus, too, it is desirable for information about the controller-set measuring items and criteria to be made available to the subject or operator upon request. Illustratively, the control unit in the operator's possession may be connected via a communication line to such data sources as an externally furnished database and a database housed in the host computer or server on the part of the controller. Such a setup allows the subject or operator to retrieve information about the relevant examination or medical care from the control unit. The retrievable information may include the content of the examination (i.e., purpose of the examination), the examination method (the manner in which the examination is to be performed), and criteria for judgment (normal values). Information may be retrieved from the data sources by use of commands set by the controller. Whereas it is feasible to incorporate in the control unit a data source in the form of, say, CD-ROMs, a wider range of applications is available when the subject or operator is allowed to have access via a communication line or network to an external data source.

It should be noted that, as mentioned above, the measurement, judgment and other functions of the control unit 14 do not presuppose the presence of the communication line 24.

The control unit 14 (control unit body 16) described above includes an identification device for identifying the subject of measurement; a criterion setting device only for use by the controller such as a doctor who is capable of making a specialized judgment on the amount of the target analyte in specimens by use of specialized knowledge about the measured results; and judgment and display device for computing measurements based on the output signals from the measuring unit 12 and for selectively displaying relevant comments about the computed measurements. Preferably, the medical measurement apparatus 10 has a storage device for storing a plurality of measurements, a questioning device for putting preliminary questions to the subject (operator), and a verification device for verifying that measurement is performed under appropriate conditions.

The identification device identifies the subject of measurement based on his identification data supplied by the operator.

Equipped with this identification device, when the medical measurement apparatus 10 of the invention allows only the identified subject, no other subjects are examined and the apparatus is arranged to accumulate measurements of only the identified subject(s).

When the medical measurement apparatus 10 deals with a plurality of subjects, the apparatus takes measurements specific to each of the individual subjects. If unnecessary measurements are taken of any subject, they cannot be examined by the apparatus and only the relevant measurements are accumulated with respect to the individual subjects.

Thus the inventive medical measurement apparatus 10 does not mix measurements of one subject with those of any other subject. With the possibility of mixed-up measurements eliminated, the controller such as the doctor is not misled to make erroneous diagnosis based on the incorrectly accumulated measurements.

The medical measurement apparatus 10 of the invention poses no specific constraints on the types of usable identification data about the subject. The identification data may preferably include personal data such as the name and the date of birth, the ID code such as a password number, the fingerprint and the voice print of each subject. The identification may be provided alternatively in the physical form of a security card or a key possessed by the subject or by the operator. No specific constraints exist on the manner of entering the identification data. That is, the ID data may be input by use of the keyboard 18, the mouse 20, a touch panel, a bar code reader; a card reader for reading IC cards, a magnetic cards or optical cards; or a disc drive for driving floppy discs, magneto-optical discs or hard discs.

In other words, the embodiment of the invention may utilize advantageously any of the diverse techniques of personal identification. However, it is preferred that the apparatus should be made unavailable for measurement unless and until both an ID card (e.g., security card) and a password code are entered. The health insurance card, driver's license, electronic medical chart or other personal identification card of the subject may use as his ID card or security card. Alternatively, the ID card may be a card issued by the controller at the time of registering the patient with the apparatus.

For the medical measurement apparatus 10 of the invention, the identification data should preferably be set by the controller alone. To have the settings of the apparatus established only by the controller requires two things: either the controller alone is allowed to make or modify the settings, or only the subject or operator authorized by the controller is to carry out the same.

These arrangements are intended to prevent the operator or any other third party from inadvertently altering the identification data or from making other careless or deliberate modifications of data.

There are no specific constraints on the manner in which to set identification data. The same methods as those cited above for entering the ID data may be utilized.

Similarly, there exist no specific limits to the way in which to limit the qualification for setting ID data only to the controller. Any one of various known methods for entering the subject's identification data such as the use of the controller's ID code may be utilized.

The criterion setting device is used only by the controller such as a doctor who has specialized knowledge on medicine and who sets the items of measurement, the criteria for judging measured results, and comments and commands about the measurements with respect to the criteria. The settings can be made for each individual subject and in consideration of the changes over time in the subject's conditions.

To make effective use of the measurements taken by the medical measurement apparatus requires selecting appropriate measuring items by taking into account the patient's pathologic conditions and symptoms, the result of the pregnancy test performed on a woman, a mother's physical conditions, and other relevant status of the subject in question.

The measurements (measured results) taken in medical examination vary depending on a number of factors. These factors include the patient's pathologic conditions, physical differences among a plurality of subjects, the number of weeks of pregnancy for a pregnant woman, and other individual circumstances of the subject in question.

The conventional medical measurement apparatuses have their measuring items established in advance and do not allow the items to be modified according to individual subjects. With all measurements displayed numerically by those apparatuses, any operator with no specialized knowledge finds it difficult to make a proper judgment on the measured results.

In the conventional medical measurement apparatuses, even where criteria for judgment (i.e., cut-off values) are established, the criteria are fixed for all potential and actual patients. The comments about measurements with respect to the criteria are limited mostly to such simple statements as "high" and "low." In such a conventional setup, the subject is unable to grasp his conditions properly.

In contrast, the medical measurement apparatus 10 of the invention allows suitable items of measurement to be selected for individual subjects by the controller.

Illustratively, the measuring items are selected by purpose: for determining pregnancy. Grasping the mother's physical conditions, and finding the patient's pathologic conditions. Appropriate criteria for judging the measured results are also set up, and a variety of comments about the measured results with respect to the criteria are provided by the controller such as doctor. Such comments provided by the controller may include: "You are in Good health," "Contact our hospital as soon as possible," "See your doctor at our hospital as soon as possible," "Take the drug," "Stop taking the drug," and "Take measurements (of another measuring item)." It is also possible to set an appointment for the next measurement or examination.

With the inventive medical measurement apparatus 10, such measuring items, criteria for judgment and comments may be set or modified as needed only by the controller such as a doctor with specialized knowledge.

Commands may be executed in place of or in addition to the comments displayed. Although the display of comments may be regarded as a kind of commands, separate commands should preferably be furnished illustratively as follows:

(1) A command may cause the apparatus to take measurements of another item X hitherto-unauthorized, triggering display of a comment "Measure X next" to prompt the operator to proceed with the measurement.

(2) Another command may cause the apparatus to transmit an alarm to the host computer of the controller, to communicate with the controller's host computer via a communication line, or to place a telephone call to the controller.

(3) On the basis of the measurements taken of the first target analyte, another command may cause the apparatus to modify the criteria for judging the second target analyte to be examined.

(4) Another command may cause the apparatus to alter the constraints on the dates on which measurement is authorized.

(5) Another command may cause the apparatus to transfer the measured results to the host computer or server on the part of the controller.

(6) Another command may cause the apparatus to call via a communication line an examination appointment status screen as well as such service programs as an examination appointment entry program from the controller's host computer or server.

(7) Another command may cause the apparatus to retrieve information from relevant data sources (e.g., database).

Execution of the above commands is desired in situations where the controller and the subject are separated over a long distance or where the measurement and the care involved are highly urgent. Where the subject or operator is not expected to seek relevant medical care promptly due to impediments such as advanced age, the controller should preferably set in advance necessary measures as commands to ensure appropriate medical care.

According to the medical measurement apparatus 10 of the invention, individual subjects are allowed to take measurements best fit for themselves inside or outside medical institutions, to receive experts' judgments on their measurements in an individually customized manner, and to take necessary action as prompted such as visits to the doctor or changes in the frequency of measurement. Measurement and medical treatment are thus made available effectively and efficiently to those who need them. The medical measurement apparatus allows the subjects to live with a sense of security at home or elsewhere by taking measurements on their own and verifying the experts' judgments on their measurements. The measured results provide a very effective aid to those engaged in taking care of the subjects. In short, the inventive medical measurement apparatus offers remotely provided, efficacious medical care to home-care situations.

Furthermore, the medical measurement apparatus 10 of the invention is far superior to conventional systems or apparatuses in providing detailed and precise control over medical measurement by the controller such as a doctor and a pharmacist with specialized knowledge about medical care. The controller can make sure that the apparatus is appropriately utilized and that incorrectly acquired measurements do not result in misdiagnosis. It is also possible to inhibit the measurement of items not authorized to a specific subject and to prevent the abuse of individually acquired measurement information.

There are no specific constraints on the manner in which to set the items of measurement, the criteria for judgment, or comments. The same methods as those cited above in connection with the entry of identification data may also be employed. It is not necessary to match one measuring item with a single criterion and a single comment; each measuring item may correspond to a plurality of criteria as well as to a plurality of comments and commands. This makes it possible to provide more precise, fine-tuned medical measurement tailored to each subject.

Likewise, no specific constraints exist on the way in which the controller alone is allowed to set the criterion setting device. As in the case of the subject's identification data and of the manner of entering such ID data, various known methods may be used, including the use of the controller's identification code to make entries into a predetermined subroutine dedicated to the controller.

Below is an example of how the controller alone is permitted to set the criterion setting device.

When a subject (e.g., patient) visits the medical institution to see the controller such as a doctor for medical examination, the controller stores into a "health care card" the items of measurement appropriate to the subject's pathologic conditions, the criteria for judging measurements, comments and commands. These settings are stored by the controller using a reader-writer or a disc drive connected to the host computer, into the card in the form of a storage medium such as an IC card or a floppy disc. At the same time, the subject's name and other basic personal data on the subject are stored into the card along with a password code chosen by the subject. Entry of the data into the storage medium by the controller requires the use of the security card possessed only by the controller, the password code known only to the controller, or both.

The controller hands the health care card thus prepared over to the relevant subject, together with the security card dedicated to that subject as needed. The subject takes his health care card home and connects it to the control unit 14 of the medical measurement apparatus 10 in his possession. Upon measurement, the measured results are written to the health care card. To carry out the measuring operations requires the use of the security card possessed only by the subject, the password code known only to the subject, or both.

The control unit 14 checks to see if the intended measurement is appropriate in view of the date and time of the measurement and of the answers to preliminary questions put to the subject. Then in accordance with the criteria set by the controller, the control unit 14 judges the measurements and displays and/or executes relevant comments and/or commands set by the controller. If the subject is unable to perform measurement on his own, an operator may take over the measuring operations from that subject.

At the time of measurement, instead of the subject selectively entering the measuring items authorized by the controller, the connected measuring unit 12 (analyzing section 12a) may alternatively discriminate and establish the appropriate measuring items automatically. The discrimination device may be any one of known devices employing output signals, bar codes and a magnetic tape used for connecting the apparatus components, for shape recognition by the analyzing section 12a, and for connection with the measuring unit 12.

The judgment and display device computes measurements from electrical signals from the measuring unit 12. Comparing the measurements with the criteria, the judgment and display device selects the appropriate comment and displays it on the display unit 20.

The judgment execution device computes measurements from electrical signals from the measuring unit 12. Comparing the measurements with the criteria, the judgment execution device selects the relevant command and causes the control unit 14 to execute that command.

The illustrated medical measurement apparatus 10 of the invention preferably comprises a storage device for storing and accumulating a plurality of measurements for each subject. The storage device is preferably constituted so that the controller retrieves the stored data as desired.

With the constitution above, the controller such as a doctor may reference the accumulated measurements for subsequent treatment or measurement. Because the medical measurement apparatus 10 of the invention uses its identification means to identify the subject for measurement, the resulting measurements will not be mixed up with measurements of any other subject. This allows the controller to pass an accurate judgment on the relevant measurements of the subject in question.

For the medical measurement apparatus 10 of the invention, the measurements or measured results include not only medically measured data but also the dates and time stamps of measurement, the measuring environment, measuring conditions, the subject's pathologic conditions, the subject's answers to preliminary questions put to him, the subject's reactions to the measuring conditions in effect, ambient information such as temperatures obtained by temperature sensors, and other information associated with the measurement.

The illustrated medical measurement apparatus 10 further includes a questioning device for putting preliminary questions to the subject in connection with the target item to be measured, and a verification device for verifying that measurement is performed under the measuring conditions established in accordance with the measuring item in effect. The questioning device and the verification device are constituted so that only the controller is authorized to set the preliminary questions as well as the measuring conditions.

The medical measurements thus taken often vary depending on the subject's conditions.

For example, measurements of urine hCG taken from trophoblastic disease vary significantly depending on the number of days that have elapsed since the subject underwent the operation. For pregnancy diagnosis, measurements of urine hCG also vary considerably depending on the number of days that have elapsed since the subject's previous menstruation period started.

Measurements of blood hPL and urine estriol taken in order to grasp the pregnant woman's condition vary quite appreciably depending on the number of weeks of her pregnancy.

Furthermore, measurements of aldosterone and plasma renin activity vary significantly depending on whether or not the subject is on an empty stomach at the time of measurement.

Meanwhile, to take measurements of stool hemoglobin requires acquiring the measurements and referring thereto every day.

To judge accurately those measurements thus requires altering or selecting the criteria for judgment (i.e., cutoff values) in accordance with the subject's condition.

The medical measurement apparatus 10 of the invention preferably puts preliminary questions to the subject with respect to the measuring items. The apparatus is constituted preferably so that, depending on the answers to the questions, the apparatus selects the criteria for judgment, comments and/or commands to be used.

For some measuring items, no measurements will be referenced and regarded as viable if the measuring conditions such as the measuring time, measuring period and temperatures are not strictly observed.

For example, measurements of aldosterone and plasma renin activity are not considered reliable if not taken early in the morning. Where instructions are to be Given to the subject for taking drugs, it should be noted that measurements of the current drug concentration in blood are dependent of the time at which the subject previously took the drug. When the medication time is entered into the system in response to a preliminary question, the doctor can subsequently Give appropriate instructions to the subject.

Thus the medical measurement apparatus 10 preferably includes a verification device for verifying that measurement is performed under predetermined conditions. If an attempt is made to conduct measurement under conditions other than those determined beforehand, the system will not let measurement be carried out or will give an alarm. If necessary, the system is constituted to give an alarm at a prescribed measuring time so as to prompt the subject to take measurements.

Preferably, only the controller is authorized to set the above-mentioned preliminary questions and measuring conditions.

The arrangements above permit the medical measurement apparatus to provide individual subjects with more fine-tuned and customized medical measurement.

There are no specific constraints on the manner in which to set preliminary questions or measuring conditions. The same methods as those cited a/Dove in connection with the entry of identification data may be utilized.

Similarly, there are no specific limits to the way in which only the controller is authorized to set the preliminary questions and measuring conditions.

Various known methods cited in connection with the subject's identification data and with the entry of such ID data, including the use of the controller's identification code, may be employed.

Where the preliminary questions are related to the passage of time specific to the subject (number of weeks of pregnancy, age, etc.), the data constituting the questions may be input and stored in advance in the control unit body 16. In operation, when the identification means identifies the subject, the system may automatically select the criteria for judgment or other relevant settings in keeping with the time-related conditions.

The preliminary questions may be concerned with other measurements such as blood or urine content measurements (urine sugar level, blood sugar level, etc.), blood pressure, and body temperature. With responses given to such preliminary questions, the controller can evaluate the criteria and judgments in more detail regarding individual subjects. Furthermore, the above setup makes it possible to furnish the operator (any one of nurses, clinical technicians, other doctors, etc.) with more precise, individually customized instructions that will lead to better treatment of each subject.

The inventive structures above also make it possible to avoid taking unnecessary measurements regarding the previously selected measuring items. This allows both the operator and the subject to bear less burden in medical care than before, and the resulting cost savings are considerable.

Where preliminary questions are put to the subject with respect to other measurements such as blood or urine components, blood pressure and body temperature, these measuring items may also be set in the medical measurement apparatus of this invention. The measuring unit for taking measurements regarding the preliminary questions may be either connected to or incorporated in the inventive medical measurement apparatus. In such cases, the medical measurement apparatus may be arranged to read automatically the measured results furnished in the manner described.

For example, C-reactive protein (CRP), representative of acute phase protein, measures high under such pathologic conditions as inflammatory disorders (infectious disease, appendicitis, pneumonia, hepatitis, etc.), injuries, the post-surgical stage, pregnancy and collagen disease.

For this reason, the measurement of CRP is not only an item used extensively for pathologic screening but also an item for which suitable criteria need to be set for individual subjects.

The inflammatory reaction of infectious diseases generally involves increases in body temperature. This means that the measurement of CRP is not mandatory where the body temperature remains below a certain level.

Illustratively, when the subject's temperature, given in response to a preliminary question or received from a temperature sensor, turns out to be lower than a level (e.g., 37.0° C.) specific to the subject, the system may be arranged to issue a comment saying that the measurement of CRP is unnecessary.

Such an arrangement allows the measurement of CRP to be skipped where appropriate even if that measurement has been established as a measuring item. ,This translates into less burden on both the operator and the subject and more savings in economic terms.

The criteria for judging CRP measurements are set suitably for individual subjects. Generally the threshold value for judgment is about 200 μg/dL for subjects 8 to 13 years old, and about 500 μg/dL for adult subjects. The threshold value should be higher for pregnant women and patients in the post-surgical stage.

When the measurements turn out to be below the threshold value for judgment, the apparatus issues a comment saying that although there is nothing unusual at present, the subject should pay attention to subsequent changes in body temperature. If the measurements are found to be higher than the threshold value, the apparatus issues a comment prompting the subject to contact the doctor at once or executes a command calling up the doctor in charge by radio pager or the like.

Shown below are tables listing typical preliminary questions, cut-off values, comments and other related data which may be furnished in connection with measuring items.

The listings are only for illustration, and they may be altered as needed by the controller in accordance with the subject's pathologic conditions and with physical differences among individual subjects.

TABLE 1

| Measuring Items | Preliminary Questions | Measurable Time | Cut-off Values | Alarm Set Up | Comment Lower Than Cut-off Values | Comment Cut-off Value or Higher |
|---|---|---|---|---|---|---|
| Urine hCG (for pregnant woman) | Select the number of weeks that elapsed since the day your previous menstruation period started. | Unrestricted | | Unnecessary | | |
| | 1. More than 3 weeks and not less than 4 weeks | | 0.5 mIU/ml | | Take measurements again nest week | See your doctor at the hospital within a week |
| | 2. More than 4 weeks and less than 5 weeks | | Lower than 0.5 mIU/ml<br>0.5 to lower than 20 mIU/ml<br>Lower than the previous measurement<br>20 mIU/ml or higher | | You are not pregnant this time<br>Contact your doctor immediately<br>Contact your doctor immediately<br>See your doctor at the hospital within a week | |
| | 3. More than 5 weeks and less than 6 weeks | | Lower than 0.5 mIU/ml<br>0.5 to lower than 100 mIU/ml<br>Lower than the previous measurement<br>100 mIU/ml or higher | | You are not pregnant this time<br>Contact your doctor immediately<br>Contact your doctor immediately<br>See your doctor at the hospital within a week | |
| (for trophoblastic disease) | Select the number of weeks that elapsed since the day you were operated on. | Unrestricted | | Unnecessary | | |
| | 1. 5 weeks after operation | | 1000 mIU/ml | | Take the next measurements 8 | Contact your doctor |

TABLE 1-continued

| Measuring Items | Preliminary Questions | Measurable Time | Cut-off Values | | Alarm Set Up | Comment Lower Than Cut-off Values | Cut-off Value or Higher |
|---|---|---|---|---|---|---|---|
| | | | | | | weeks after operation | immediately |
| | 2. 8 weeks after operation | | 100 mIU/ml | | | Take the next measurements 20 weeks after operation | Contact your doctor immediately |
| | 3. 20 weeks after operation | | 0.5 mIU/ml | | | Excellent recovery. See your doctor at the hospital on your next appointed date. | Contact your doctor immediately |
| Urine LH | Did you take measurements yesterday? | 04:00 to 08:00 | | | Unne-cess-ary | | |
| | 1. No, I didn't. | | 20 mIU/ml | | | Take measurements again tomorrow | Ovulation is expected within 48 hours. Take measurements again tomorrow. |
| | | | Yesterday's Value | This Time Value | | | |
| | 2. Yes, I did. | | Lower than 20 mIU/ml, Lower than 20 mIU/ml, 20 mIU/ml or higher, 20 mIU/ml or higher, | Lower than 20 mIU/ml 20 mIU/ml or higher Lower than 20 mIU/ml 20 mIU/ml or higher | | Take measurements again tomorrow Ovulation is expected within 48 hrs. Ovulation is expected within 24 hrs. Ovulation is expected within 36 hrs. | |

TABLE 2

| Measuring Items | Preliminary Questions | Measurable Time | Cut-off Values | | Alarm Set Up | Comment Lower Than Cut-off Values | Cut-off Value or Higher |
|---|---|---|---|---|---|---|---|
| Blood progesterone | Select the number of weeks of your pregnancy. | Unrestricted | | | | | |
| | 1. 4 to 9 weeks | | 15 ng/ml | | | Take measurements again 4 weeks later | Contact your doctor immediately |
| | 2. 10 to 15 weeks | | 20 ng/ml | | | Normal progress. See your doctor at the hospital on your next appointed date. | Contact your doctor immediately |
| Stool hemoglobin | Did you take measurements yesterday? | Unrestricted | | | | | |
| | 1. No, I didn't. | | 50 ng/ml | | | Take measurements again tomorrow | |
| | | | Yesterday's Value | This Time Value | | | |
| | 2. Yes, I did. | | Lower than 50 ng/ml, | Lower than 50 ng/nl | | Normal. Take measurements again 6 months later | |
| | | | Lower than 50 ng/nl, | 50 ng/ml or higher | | Take measurements again tomorrow | |
| | | | 50 ng/nl or higher, | Lower than 50 ng/ml | | Take measurements again tomorrow | |
| | | | Lower than 50 ng/ml | 50 ng/ml or higher | | See your doctor at the hospital within a week | |
| | 3. Yes, yesterday and the day before yesterday | | 50 ng/ml | | | Normal. Take measurements again 3 months later | See your doctor at the hospital within a week |

TABLE 3

| Measuring Items | Preliminary Questions | Measurable Time | Cut-off Values | Alarm Set Up | Comment Lower Than Cut-off Values | Comment Cut-off Value or Higher |
|---|---|---|---|---|---|---|
| Blood hPL | Select the number of weeks of your pregnancy. 1. 6 to 9 weeks 2. 10 to 13 weeks 3. 14 to 18 weeks | Unrestricted | 0.01 μg/mL 0.16 μg/mL 0.64 μg/mL | Unnecessary | Contact your doctor immediately | Take measurements again next week |
| Urine estriol | Select the number of weeks of your pregnancy. 1. 32 to 36 weeks 2. 37 to 38 weeks 3. 39 to 41 weeks | Unrestricted | 5 mg/L 10 mg/L 25 ng/L | Unnecessary | Contact your doctor immediately | Take measurements again next week |
| Aldoserone | Are you taking this measurement after at least 30 minutes of rest on an empty stomach? YES NO | 04:00 to 08:00 | 130 ng/mL 210 ng/mL | Necessary | Normal | Contact your doctor immediately |
| Plasma renin activity | Are you taking this measurement after at least 30 minutes of rest on an empty stomach? YES NO | 04:00 to 08:00 | 4.4 ng/mL 10.5 ng/mL | Necessary | Normal | Contact your doctor immediately |
| ASO | Select the subject's age bracket. 1. Preschool child 2. School child 3. Adult | Unrestricted | 250 U 330 U 250 U | Unnecessary | Normal value, though, take measurements again next week to make sure | Contact your doctor immediately |

TABLE 4

| Measuring Items | Preliminary Questions | Measurable Time | Cut-off Values | Alarm Set Up | Comment Lower Than Cut-off Values | Comment Cut-off Value or Higher |
|---|---|---|---|---|---|---|
| Blood CEA | Your scheduled day of measurement is December 10, 1993. | Unrestricted | 5 ng/mL | Unnecessary | Normal value. Take measurements again on the next scheduled day January 10. | See your doctor at hospital within a week. |
| | When try to take measurements before the scheduled day of measurement | | | | The system displays a comment saying "Today is not your scheduled day of measurement yet. Wait until December 10." The system is not operable for measurement. | |
| | When try to take measurements after the scheduled day of measurement | | | | The system displays a comment saying "Although today is past your scheduled day of measurement, you can proceed with measurement now. Try to be on time next time." The system is for measurement. | |
| Blood AFP | Your scheduled day of measurement is December 10, 1993. | | 20 ng/mL | Unnecessary | Normal value. Take measurements again on the next scheduled day, January 10. | See your doctor at the hospital within a week. |
| | When try to take measurements before the scheduled day of measurement | Unrestricted | | | The system displays a comment saying "Today is not your scheduled day of measurement yet. Wait until December 10." The system is not operable for measurement. | |

TABLE 4-continued

| Measuring Items | Preliminary Questions | Measurable Time | Cut-off Values | Alarm Set Up | Comment Lower Than Cut-off Values | Cut-off Value or Higher |
|---|---|---|---|---|---|---|
| | When try to take measurements after the scheduled day of measurement | | | | The system displays a comment saying "Although today is past your scheduled day of measurement, you can proceed with measurement now. Try to be on time next time." The system is for measurement. | |

As mentioned above, the medical measurement apparatus 10 of the invention allows the controller to alter as needed the criteria for judgment, comments, and preliminary questions depending on the subject's pathologic conditions and on physical differences among subjects.

For example, as shown in Table 4 above, the cut-off value of blood CEA measurements is usually 5 ng/ml. However, if the mean value ± standard deviation of blood CEA measurements over a certain past period was 3.0±1.0 ng/ml, the controller may alter the cut-off value to 4 ng/ml. This ensures a more accurate measurement.

In the example of Table 1 above, the urine LH concentration is allowed to be measured between 4:00 and 8:00 a.m., and the criteria for judgment (cut-off values) center on 20 mIU/ml.

It may happen that the urine LH concentration measurements over the past three months have indicated that the urine LH concentration during ovulation of a particular subject who wants to become pregnant is lower than that of the average woman (20 mIU/ml or higher). With the default settings in effect, it is difficult for the subject in question to find the peak urine LH concentration during ovulation. In that case, the measurable time may be set alternatively for 4:00 to 8:00 as well as for 16:00 to 20:00, the cut-off values may be supplemented with a value of 10 mIU/ml, and the comments may be modified as shown below. These modifications allow the subject to find more precisely the peak urine LH concentration during ovulation.

Preliminary Questions
1. Is this your first measurement?
2. Is this your second or subsequent measurement?
Cut-off Values and Comments
If your answer to preliminary question 1 is "YES":
(Cut-off values): Lower than 10 mIU/ml
(Comment): Take measurements again 12 hours later.
(Cut-off values): 10 mIU/ml or higher, lower than 20 mIU/ml
(Comment): Ovulation is expected within 48 hours. Take measurements again 12 hours later.
(Cut-off values): 20 mIU/ml or higher
(Comment): Ovulation is expected within 24 hours.
If your answer to preliminary question 2 is "YES":
(Cut-off values): 20 mIU/ml or higher
(Comment): Ovulation is expected within 24 hours.
(Cut-off values): Lower than 10 mIU/ml both last time and this time
(Comment): Take measurements again 12 hours later.
(Cut-off values): Lower than 10 mIU/ml last time, 10 mIU/ml or higher and lower than 20 mIU/ml this time
(Comment): Ovulation is expected within 48 hours.
(Cut-off values): 10 mIU/ml or higher last time, equal to or lower than previous measurement this time
(Comment): Ovulation is expected within 24 hours.
(Cut-off values): 10 mIU/ml or higher last time, equal to or higher than previous measurement and lower than 20 mIU/ml this time
(Comment): Ovulation is expected within 36 hours.

Regarding the urine hCG measurements for patients with trophoblastic disease shown in Table 1 above, the criteria for judgment and the comments are set in accordance with the number of weeks that elapsed since the day the subject was operated on. It may happen that when the patient with trophoblastic disease is apparently in remission, urine hCG measurements are desired to be taken to make sure that the patient has not relapsed. In that case, the preliminary questions, measurable time, cut-off values and comments in Table 1 may be modified as follows:

Measurable Time
4:00 to 8:00 a.m.
Preliminary Questions
1. Is this your first measurement?
2. Is this your second or subsequent measurement?
Cut-off Values and Comments
If your answer to preliminary question 1 is "YES":
(Cut-off values): Lower than 1 mIU/ml
(Comment): Take measurements again 2 week later.
(Cut-off values): 1 mIU/ml or higher
(Comment): See your doctor at our hospital within a week.
If your answer to preliminary question 2 is "YES":
(Cut-off values): Lower than 0.5 mIU/ml last time, less than 5 mIU/ml this time
(Comment): Take measurements again 4 weeks later.
(Cut-off values): Lower than 0.5 mIU/ml last time, 0.5 mIU/ml or higher this time
(Comment): See your doctor at the hospital within a week.
(Cut-off values): 0.5 mIU/ml or higher last time, lower than previous measurement this time
(Comment): Take measurements again 4 weeks later.
(Cut-off values): Equal to or higher than 0.5 mIU/ml last time, equal to or higher than previous measurement this time
(Comment): See your doctor at our hospital within a week.

How the medical measurement apparatus 10 of the invention is illustratively operated will now be described with reference to the flowcharts of FIG. 6 (controller's operations) and FIG. 7 (operator's operations).

Initially, the controller such as a doctor with specialized knowledge sets up the medical measurement apparatus 10 by inputting thereto various measurement-related requirements such as measuring items and criteria for judgment for individual subjects.

Figure 6:
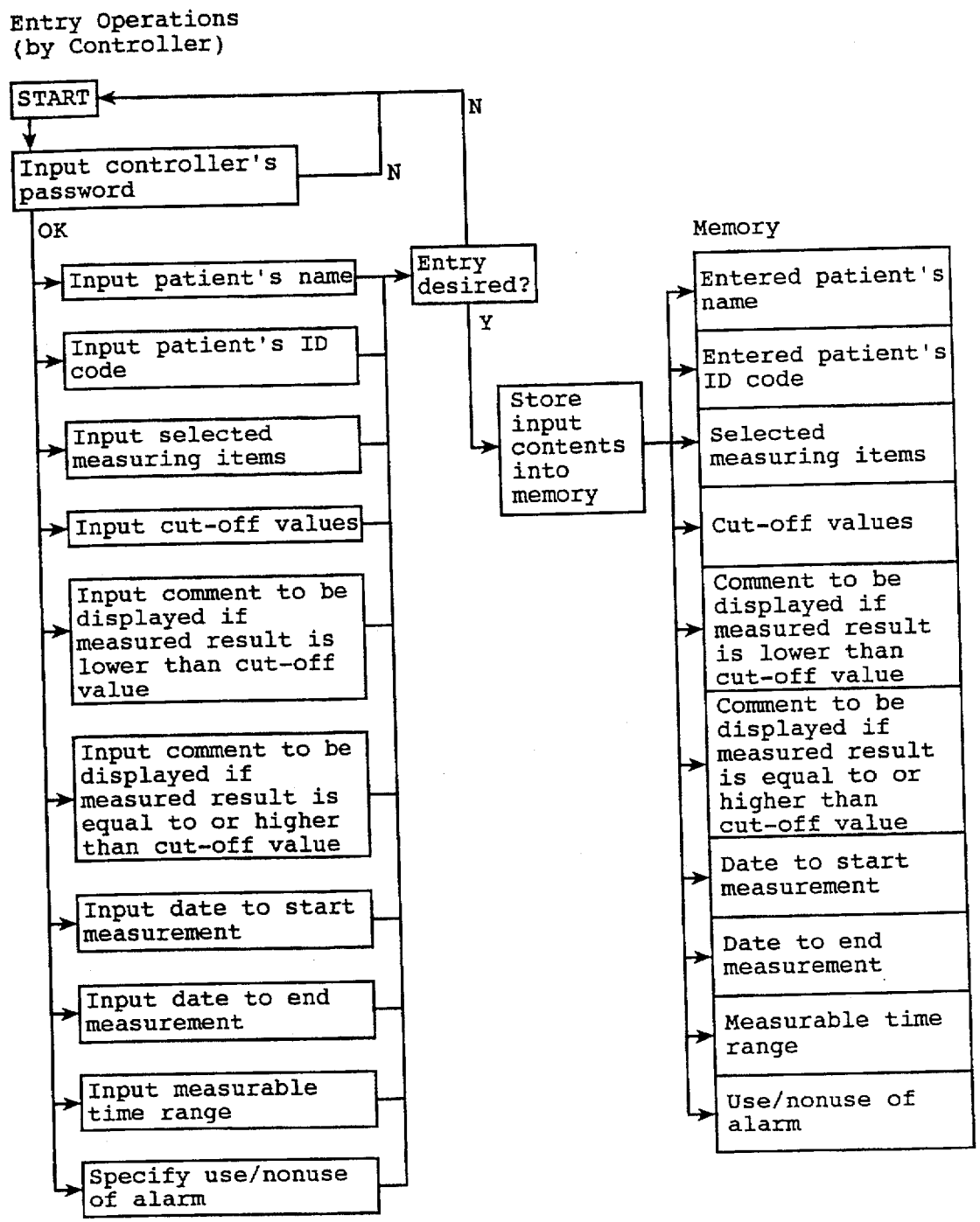
FIG. 6 is a flowchart of an example of typical steps carried out by the controller of the embodiment.

In the example of FIG. 6, the controller first enters an identification signal such as his password number to get the apparatus ready for entry Of the measurement requirements. Then with each particular subject in mind, the controller enters into the apparatus the subject's name (patient's name), the subject's ID code, an item or items of measurement, criteria (cut-off values) for judging measurements regarding the specified measuring item(s), comments to be issued when the measured results are above or below the cut-off values, the date for starting measurement, the date for ending measurement, a permitted period for measurement, and the execution or nonexecution of a measuring time alarm, etc.

If the controller does not enter specific values or comments for any measuring item, the apparatus automatically establishes preset data by default.

These settings and entries are made by use of the keyboard 18 attached to the control unit 14. All data entered through the keyboard 18 is displayed on the display unit 22 for verification (this also applies when the patient operates the apparatus, as will be described later).

As already described, these settings and entries may be recalled and altered as needed by the controller.

Each of the entries is stored into the corresponding memory in the control unit body 16. For example, the patient's name and the patient's ID code are stored into the memory for the identification device; the measuring items, cut-off values and comments are stored into the memory for the criterion setting device; and the times for starting measurement are stored into the memory for the verification device.

When the medical measurement apparatus 10 is set up in the above manner, the apparatus is ready for use by the patient.

When the medical measurement apparatus 10 starts to be used, an alarm marking the time for starting measurement is activated if the controller has set the apparatus for alarm activation. With the alarm activated, the apparatus enters a start-up state.

In the start-up state, the patient (subject and operator) enters his name, his ID code and the relevant measuring items. When a given item is entered, the control unit body 16 retrieves the item from the corresponding memory for display and verification.

If any entered item is not correct, an alarm beep is sounded and the start-up state is reached again.

When the entered item is correct, the patient's past measured results of this item are displayed on the display unit 22.

The date of measurement is verified next. If the entered date is not correct, the alarm beep is sounded and the start-up state is reached again.

When the entered date of measurement is correct, the display unit 22 gives a comment saying that the date is correct. A specimen is then supplied to the measuring unit 12 and measurement is started.

The output signals (electrical signals) from the measuring unit 12 are sent to the judgment and display means of the control unit body 16.

The judgment and display device, computes measured results from the received output signals, selects the relevant comment based on the measured results and according to the criteria for judgment, and displays the comment on the display unit 22. At the same time, the date of measurement, the measured results and the other related data are stored into the storage device.

Alternative ways to operate the medical measurement apparatus 10 of the invention will now be described with reference to the flowcharts of FIG. 8 (controller's operations) and FIG. 9 (operator's operations). These examples are ones in which preliminary questions are put to the person operating the apparatus and the apparatus proceeds with measurement in accordance with the answers given in reply to these questions.

Figure 7:
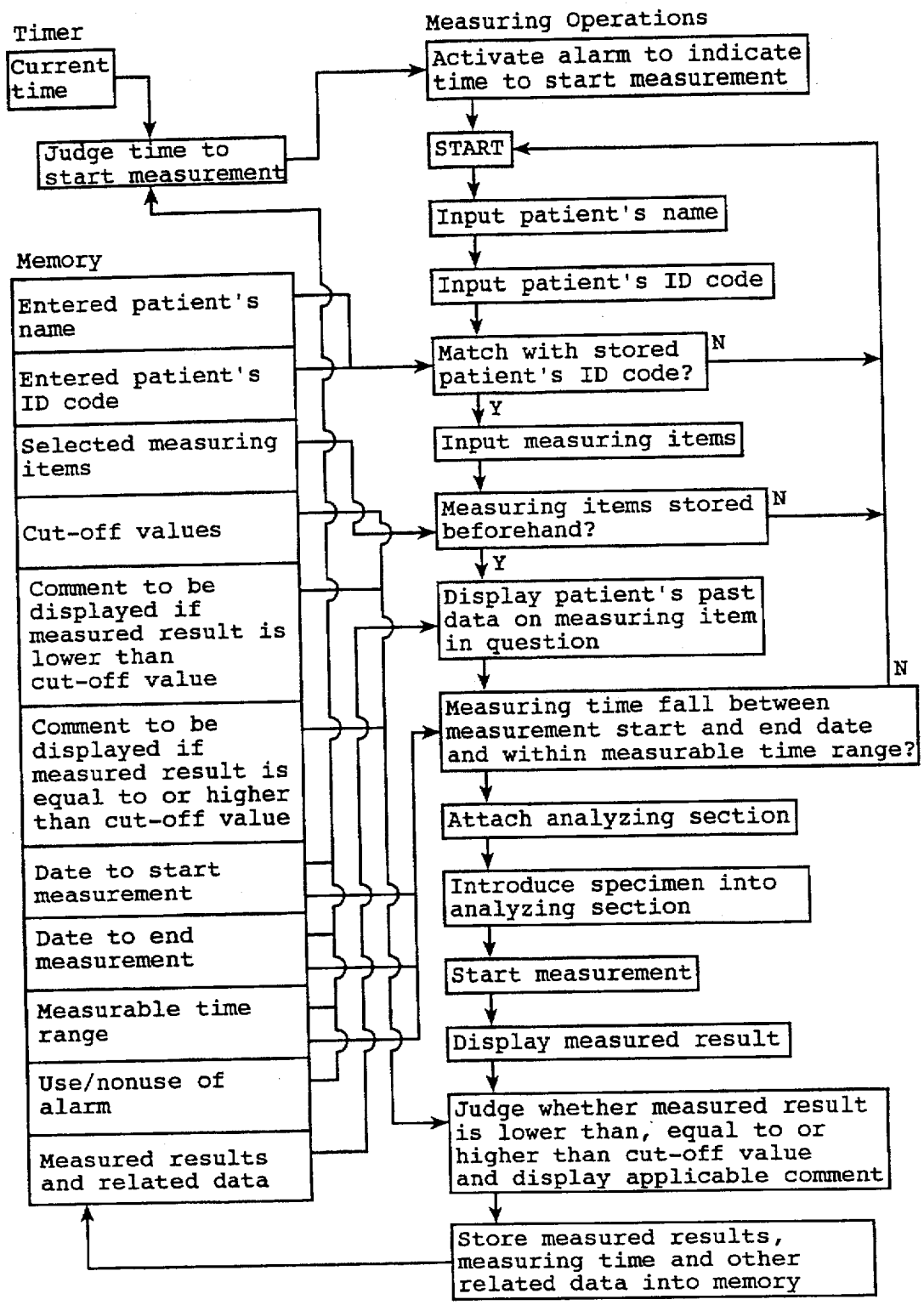
FIG. 7 is a flowchart of an example of typical steps performed by the operator of the embodiment.
Figure 8:
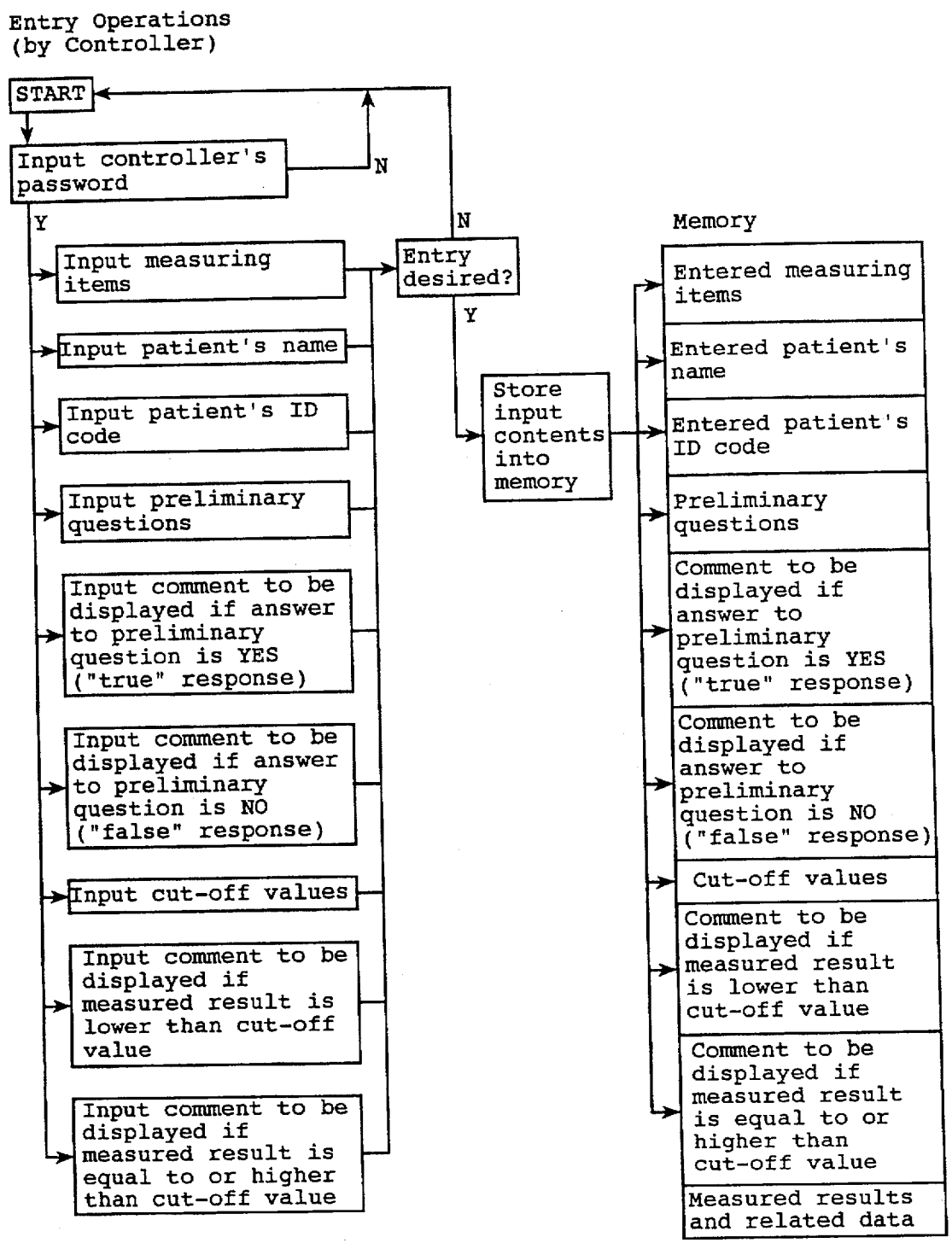
FIG. 8 is another flowchart of an example of typical steps carried out by the controller of the embodiment.
Figure 9:
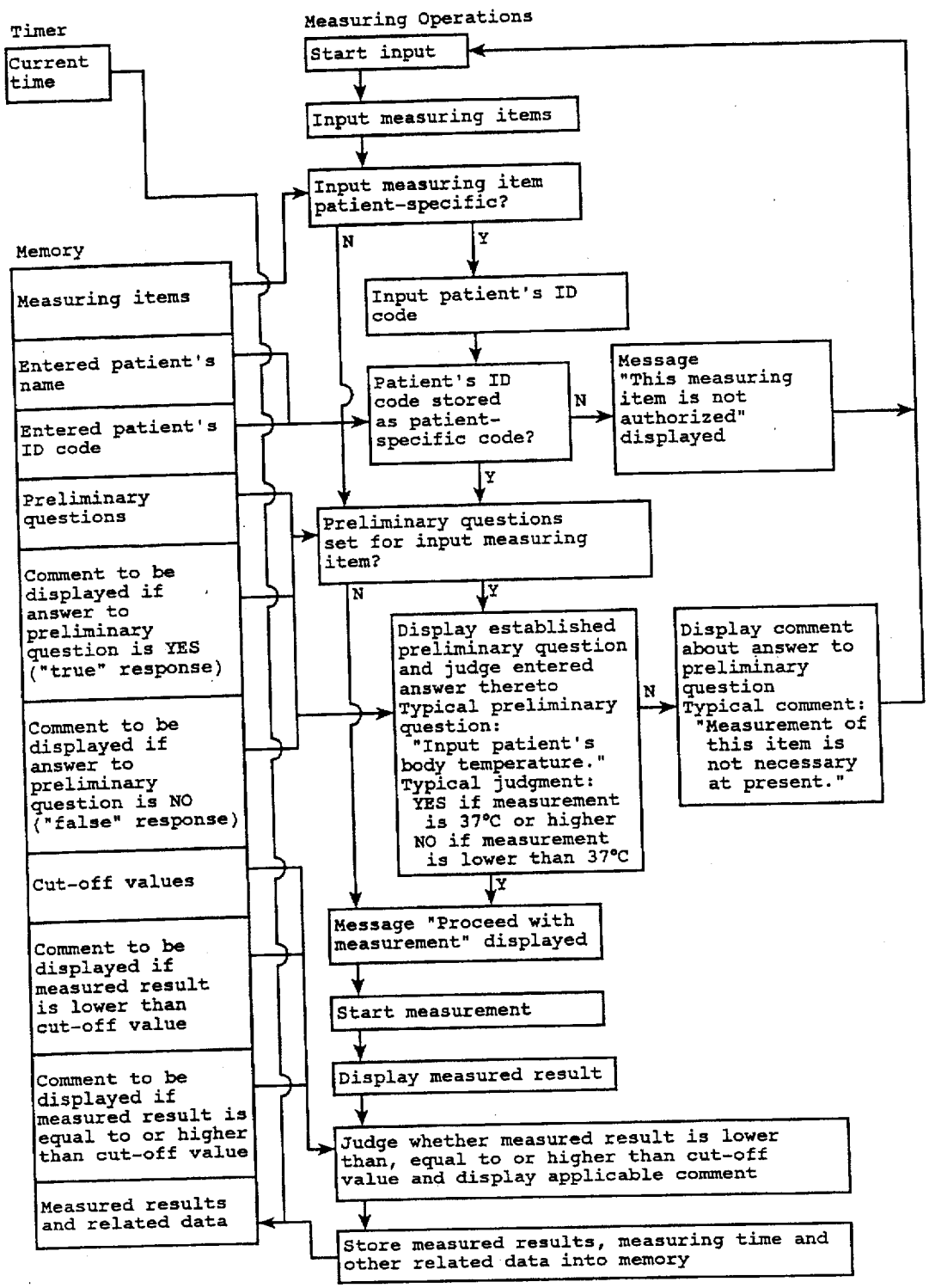
FIG. 9 is another flowchart of an example of typical steps conducted by the operator of the embodiment.

The examples in FIGS. 8 and 9 are primarily the same as those of FIGS. 6 and 7 except that the preliminary questions are asked. The description that follows will center on the differences between the two groups of examples (the same will also apply to examples of FIGS. 10 through 13 to be explained later). The controller, as in the earlier examples, first enters the patient's ID code or other appropriate identification data, as well as preliminary questions and comments about possible answers to the preliminary questions (judgments). Later, the operator enters the measuring item(s) and the patient's ID code to check if the entered item is correct. In this example, the input of the patient's name is replaced by that of the patient's ID code and is thus omitted. Then a check is made to see if there are any preliminary questions that have been set. If such questions exist, they are displayed on the display unit 22. The operator enters answers to the preliminary questions, and proceeds with measurement by following predetermined procedures or in accordance with the instructions from the apparatus, as shown in the flowchart.

Figure 10:
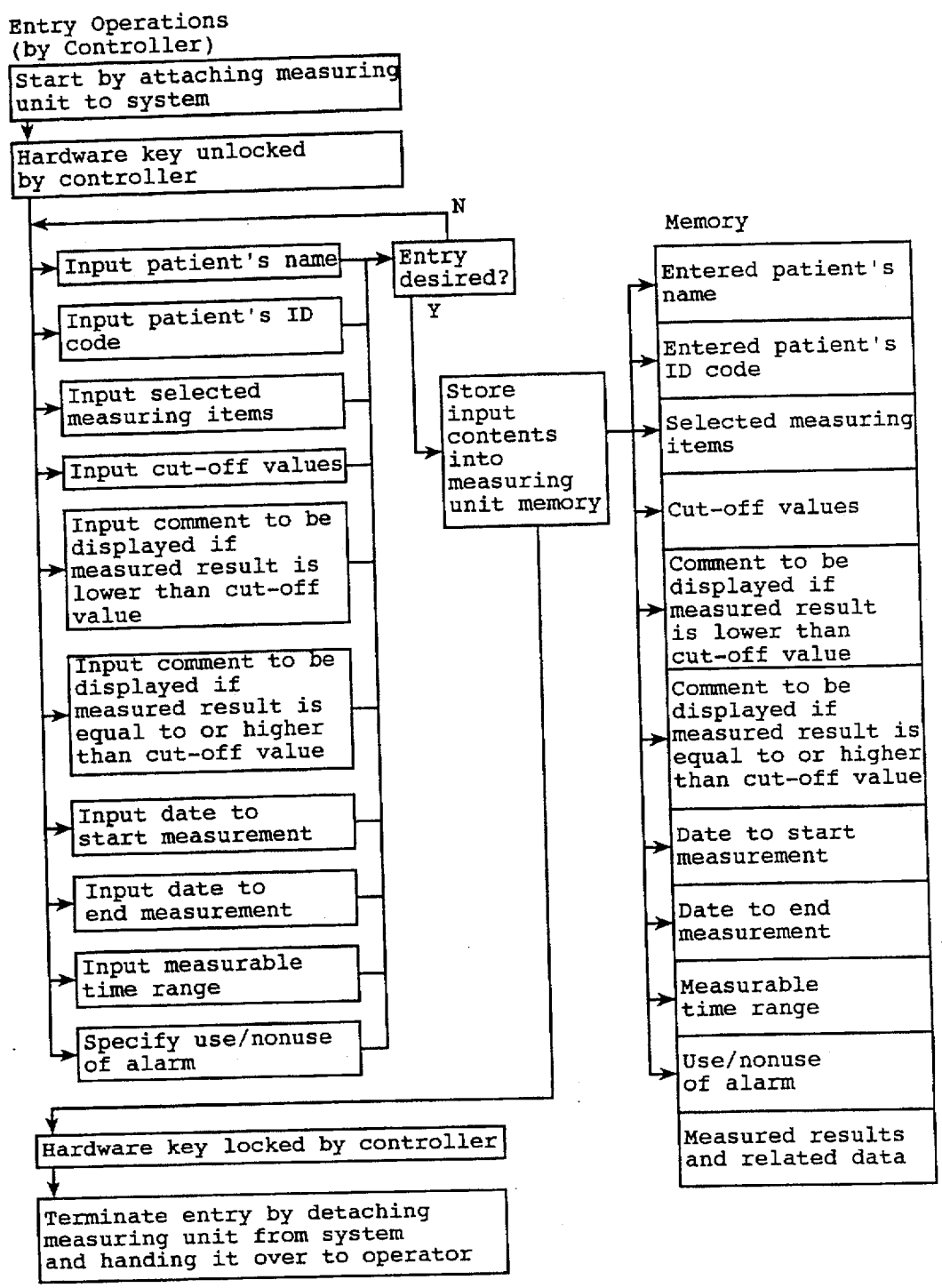
FIG. 10 is another flowchart of an example of typical steps followed by the controller of the embodiment.
Figure 11:
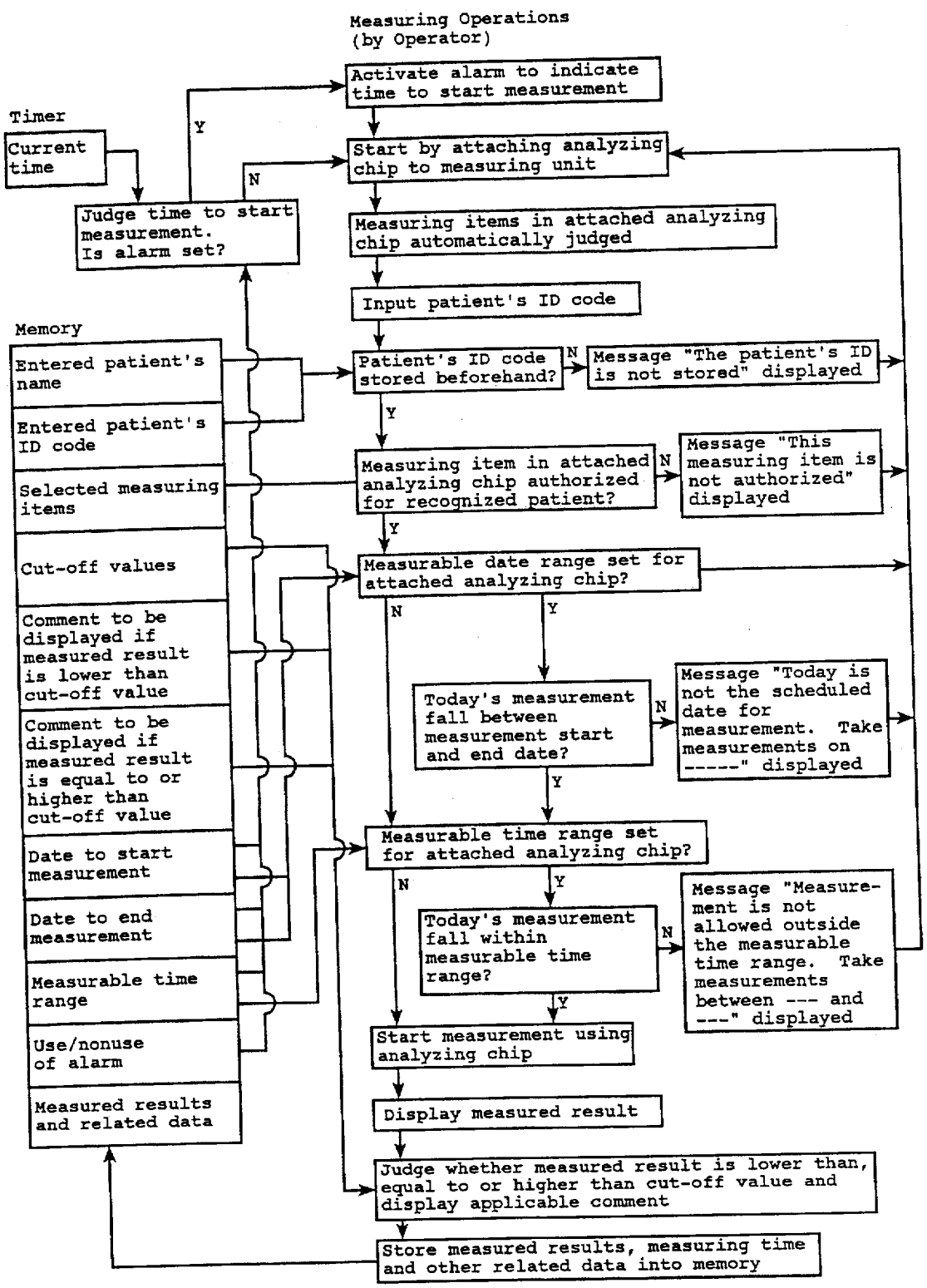
FIG. 11 is another flowchart of an example of typical steps carried out by the operator of the embodiment.

Other alternative ways to operate the medical measurement apparatus 10 of the invention will now be described with reference to the flowcharts of FIG. 10 (controller's operations) and FIG. 11 (operator's operations). These examples are ones in which the settings of measurable dates and times vary with the measuring items.

The controller unlocks the hardware (i.e., control unit body 16) using his password number or ID code, and enters the patient's ID code, the measurable items, measurement starting date, and other appropriate settings. In this example, the setting of the patient's name is replaced with the patient's ID code and is omitted. Then a check is automatically made to see if each measuring item is correct. The manner of conducting the check is the same as that discussed above in connection with attaching the measuring chip (i.e., analyzing section 12a or output section 12b) to the medical measurement apparatus 10. The comment to be displayed in any measuring item is stored in advance.

The operator connects the measuring chip to the system and enters the patient's ID code. The system then verifies the patient's ID code, the measuring items (automatically checked by the measuring chip as mentioned), and the date and time of measurement, and passes judgments thereon. Where necessary, the display unit 22 displays comments relevant to these judgments. When all measuring conditions are found to match the set conditions, the operator proceeds with measurement by following predetermined procedures or according to the instructions given by the apparatus.

Figure 12:
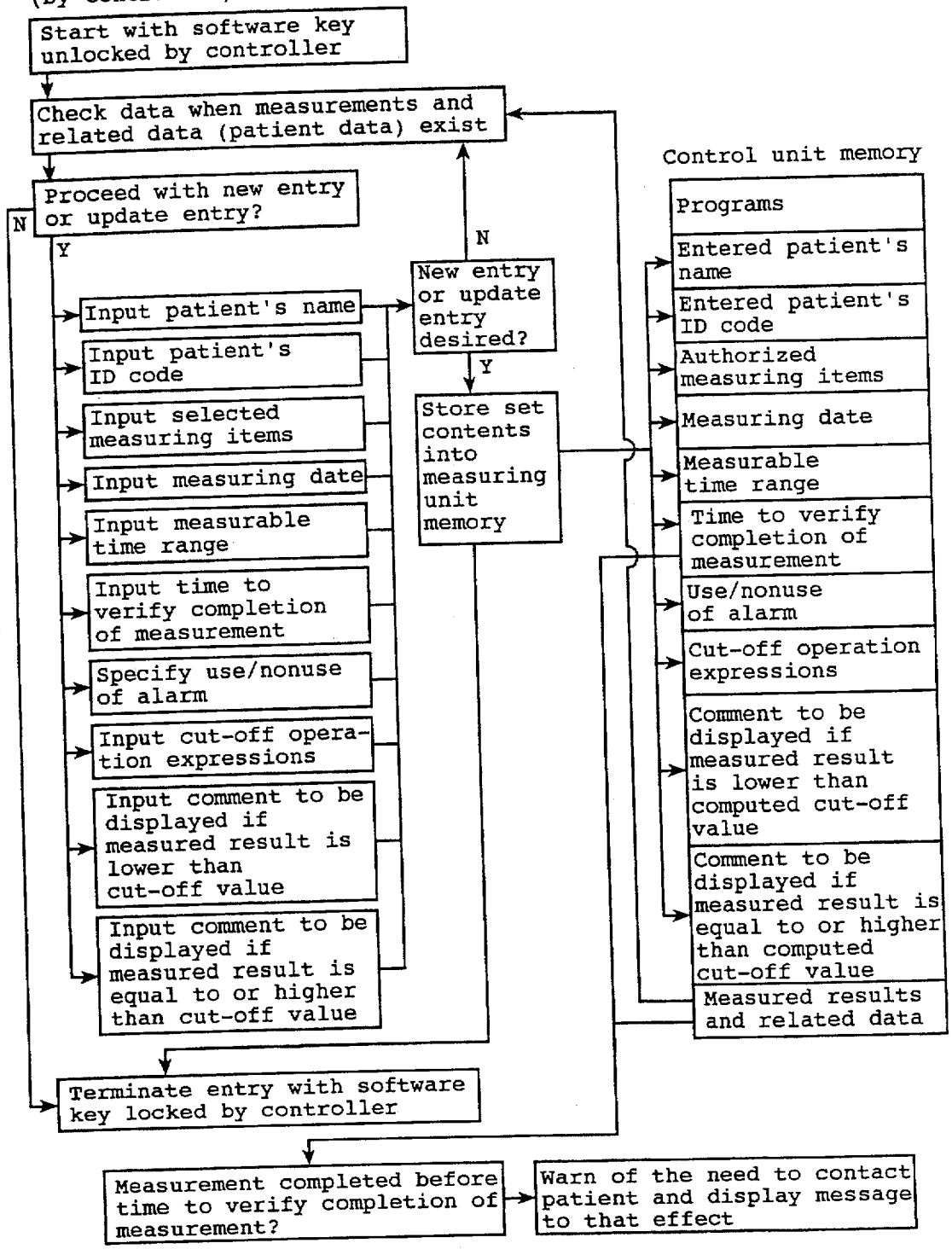
FIG. 12 is another flowchart of an example of typical steps conducted by the controller of the embodiment.
Figure 13:
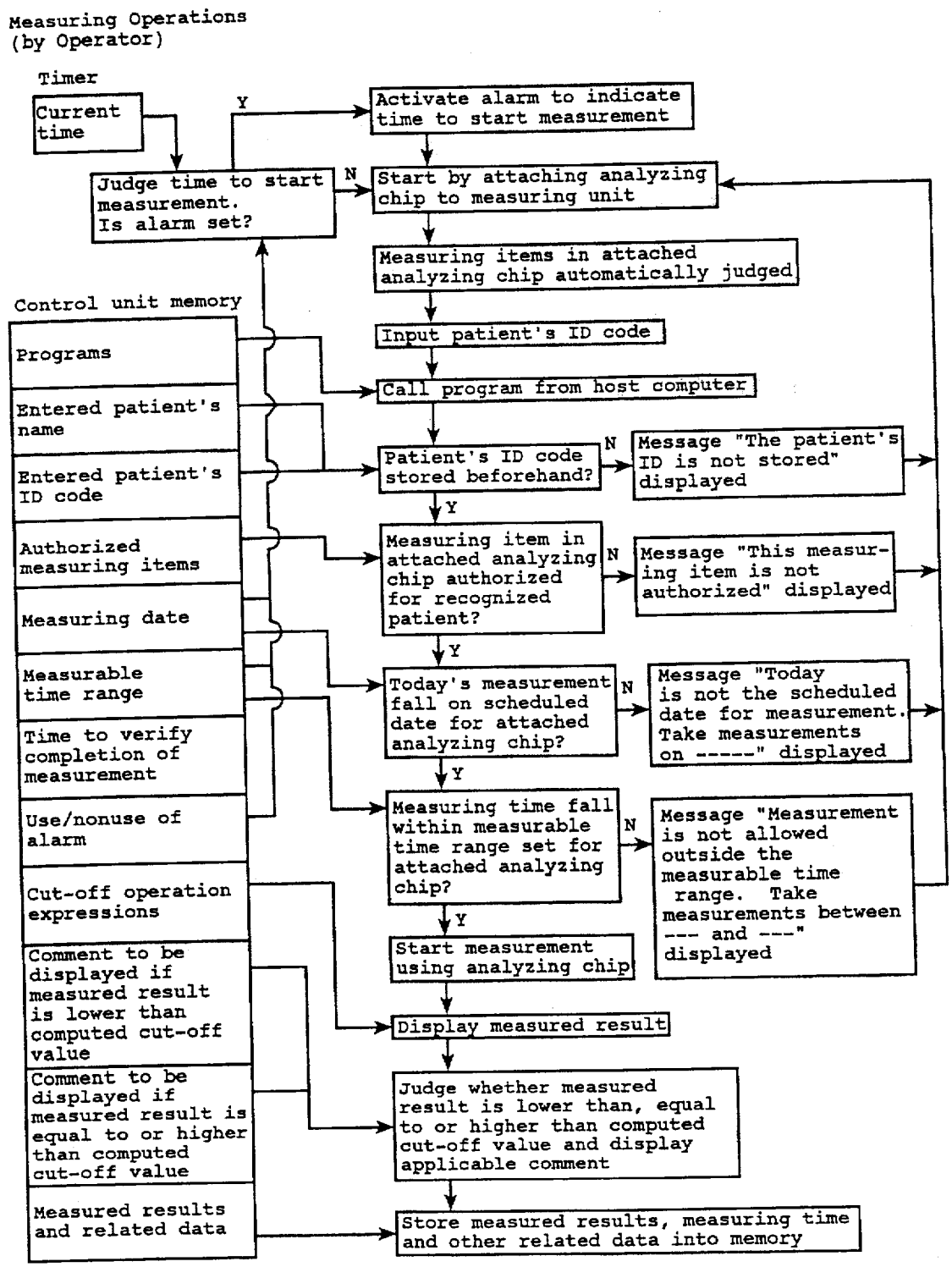
FIG. 13 is another flowchart of an example of typical steps performed by the operator of the embodiment.

Further alternative ways to operate the medical measurement apparatus 10 of the invention will now be described with reference to the flowcharts of FIG. 12 (controller's operations) and FIG. 13 (operator's operations). These examples are ones in which the medical measurement apparatus 10 is connected to the host computer 100 on the controller's side and in which the cut-off values for judging measured results are replaced by numerical operation expressions for cut-off purposes. The measured results are judged based on the computed values, and comments are displayed accordingly.

The controller unlocks the software of the host computer using his password number or ID code. If there exists data representing past measurements, the controller may examine that data. The controller then specifies either new entry or entry modification. If any of the stored settings need to be modified in accordance with the result of examination of the patient's data, the controller alters the relevant measuring items, cut-off numerical operation expressions and other settings. For the new entry of settings, the controller inputs a new patient's name, measuring items and other data. The controller then locks the software.

The operator connects the measuring chip to the apparatus and enters the patient's ID code. This causes the apparatus to verify the patient's ID code, the measuring items (automatically checked by the measuring chip), date and time of measurement, and other settings. Comments relevant to the judgments by the apparatus are displayed on the display unit 22. When all conditions are found to match the set conditions, the operator proceeds with measurement by following predetermined procedures or according to the instructions provided by the apparatus.

Other alternative ways to operate the medical measurement apparatus 10 of the invention will now be described with reference to typical displays on the display unit 22 shown in FIG. 14,(a control panel in effect when the controller starts entering settings), FIG. 15 (a control panel in effect when the controller enters measurement-related settings), FIG. 16 (a control panel in effect when the operator starts measurement), and FIG. 17 (a control panel showing the controller's comment when the operator ends measurement). The medical measurement apparatus 10 shown illustratively herein has an LCD acting as a control panel on the display unit 22 (FIG. 1). The keyboard may be used to enter characters into the fields and the mouse may be operated to manipulate push virtual buttons on the displayed control panel.

Figure 14:
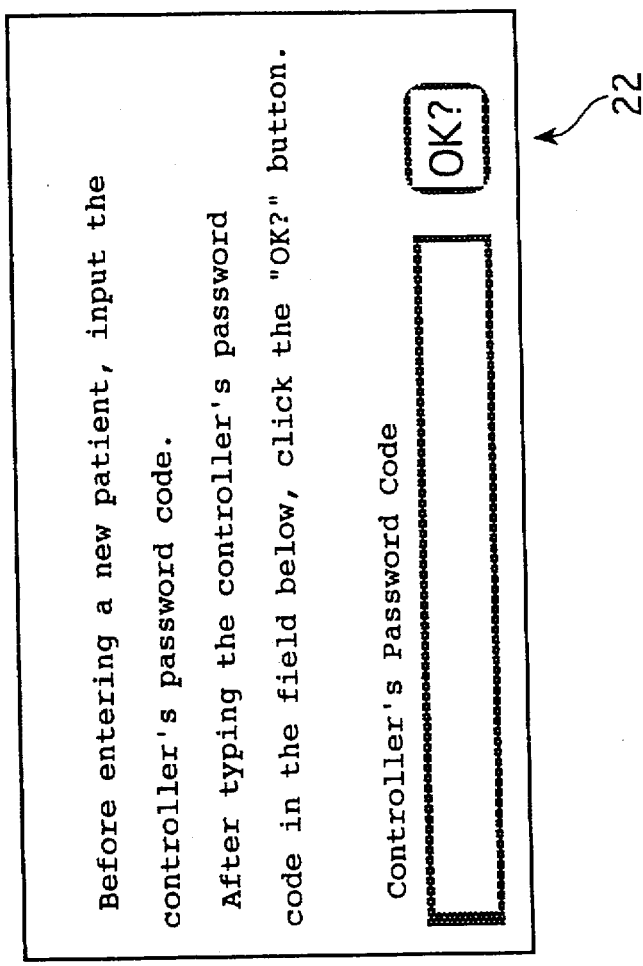
FIG. 14 is a schematic view of an example of the typical display (on the control panel) in effect when the controller starts making entries into the embodiment of FIG. 1.

When the controller starts an entry procedure by activating a group of subject entry commands, the display unit 22 displays the control panel of FIG. 14 requesting the input of the controller's password code. When the controller's password code is entered through the keyboard and the "OK?" button is clicked with the mouse, the control unit compares the input code with the stored password code. If the input code is found to coincide with the stored password code, the display unit 22 displays the control panel of FIG. 15 for the entry of settings. If the input code and the stored password code fail to coincide with each other, the start-up state is reached again and another input of the controller's password code is requested.

Figure 15:
FIG. 15 is a schematic view of an example of the typical display (on the control panel) in effect when the controller sets measurements in the embodiment.
Figure 16:
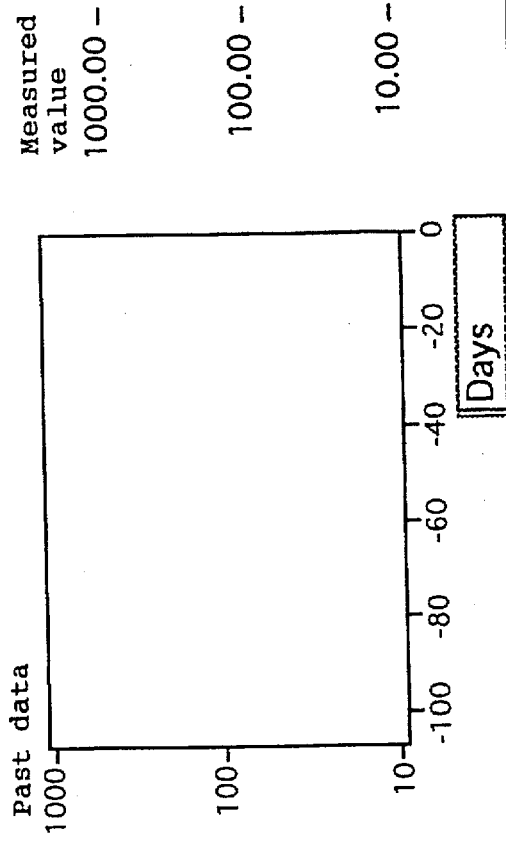
FIG. 16 is a schematic view of an example of the typical display (on the control panel) in effect when the operator starts making measurement using the embodiment.

The control panel of FIG. 15 comprises a subject (patient) name input field, a subject ID (password) code input field, a ring switch for selecting the target analyte to be analyzed, an entry date indication field, an entry time indication field, a criterion (cut-off) setting slide switch, a comment input field for giving a comment when the measured result is equal to or higher than the criterion, a comment input field for giving a comment when the measured result is lower than the applicable criterion, a ring switch for Setting date to permit start of measurement (day, month, year), a ring switch for setting date to permit the end of measurement (day, month, year), a ring switch for setting a day of the week on which to permit measurement, a ring switch for setting a measurable time range, an alarm setting push button, an entry verification push button, and an input field in which to enter the controller's password code at the time of data entry.

In the example of FIG. 15, a patient named "T. Yamauchi" is entered with a code name "CHU1." The target analyte to be analyzed is set for "urine hCG" and the criterion for measured result is set for "50 IU/L." When the measured result exceeds the established criterion, the control panel is set to display a comment saying, "Congratulations. You are probably pregnant. Contact your doctor as soon as possible at the M hospital (call 03-XXXX-XXXX)." When the measured result is lower than the applicable criterion, the control panel is set to display a comment saying, "You are probably not pregnant. If you are in doubt, contact your doctor any time at the M hospital (call 03-XXXX-XXXX)." The date on which measurement is allowed to start is set for "Now." The date on which measurement is allowed to end is set for "October 31 this year." The day of the week on which to conduct measurement is not restricted, whereas the measurable time range is limited to the early morning between 4:00 and 8:00. The alarm is turned off. When these settings are entered and considered satisfactory, the controller enters his password code and pushes the "entry verification push button." This causes the control unit 14 to store the settings into the storage device.

The operator, for her part, operates the control unit 14 on the basis of the settings entered by the controller. The control panel of FIG. 16, in effect when the control unit 14 starts measurement, presupposes that the operator and the subject are the same person. That is, when the control unit 14 starts measurement, the display unit 22 displays the control panel of FIG. 16. This control panel comprises a ring switch for selecting the subject name, a subject password code input field, a measurement date indication field, a measurement time indication field, a ring switch for selecting the target analyte to be analyzed, a measured result indication field, a graphic indicator for showing measured results, a comment indication field ("Remarks" field), a Graphic indicator for showing her past data, a ring switch for determining whether or not to save measured results, and a push button for deciding whether or not to perform the next measurement continuously.

The operator cannot start measurement unless he selects the patient's name, enters the correct subject ID code, and chooses the target analyte allowed for measurement. Furthermore, the intended measurement cannot be started if it does not fall on the date of measurement authorized by the controller or within the permitted time range for measurement. When the entries made by the operator are correct and satisfy the conditions set by the controller, the graphic indicator for showing past data displays the subject's past measurement data in the form of a simple line chart, with the "Remarks" field giving a message prompting the operator to start measurement. If the intended measurement is not permitted for some reason, that reason is displayed in the "Remarks" field and the control unit returns to the start-up state. When measurement is permitted, the operator gets the hCG analyzing section (shown in FIGS. 3 and 4) placed into the measuring unit (because "urine hCG" is selected as the target analyte to be analyzed for this example), introduces a urine specimen into the analyzing section, and starts measurement. The measured result is displayed five minutes later, and the "Remarks" field displays a controller-set relevant comment in accordance with the criteria set by the controller.

Figure 17:
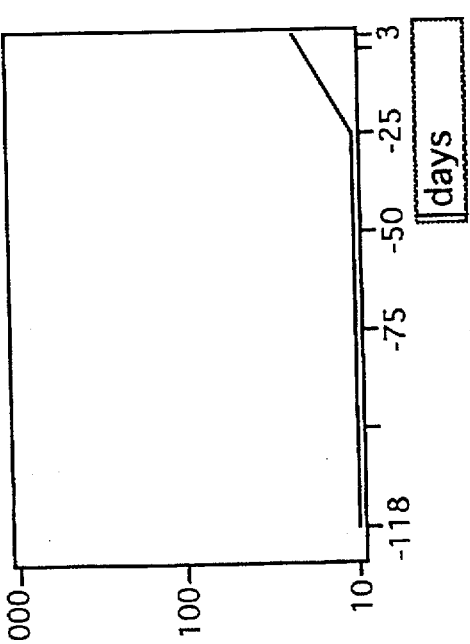
FIG. 17 is a schematic view of an example of the typical display (on the control panel) in effect when the operator terminates measurement with the embodiment.

When measurement is ended, the display unit 22 displays the control panel of FIG. 17. In this example, the measurement taken is 200 IU/L, a value exceeding the applicable criterion. The control panel thus displays a comment set by the controller in advance saying, "Congratulations. You are probably pregnant. Contact your doctor at the M hospital (call 03-XXXX-XXXX) as soon as possible."

Typical operating procedures of the medical measurement apparatus 10 of the invention as well as the internal workings of the control unit 14 will now be described with reference to FIGS. 18 (on the controller's side) and FIG. 19 (on the operator's side). The operations in FIG. 18 correspond to the flowchart of FIG. 6 as well as to the control panels (displayed on the display unit 22) of FIGS. 14 and 15, and the operations in FIG. 19 correspond to the flowchart of FIG. 7 as well as to the control panels of FIGS. 16 and 17.

Figure 18:
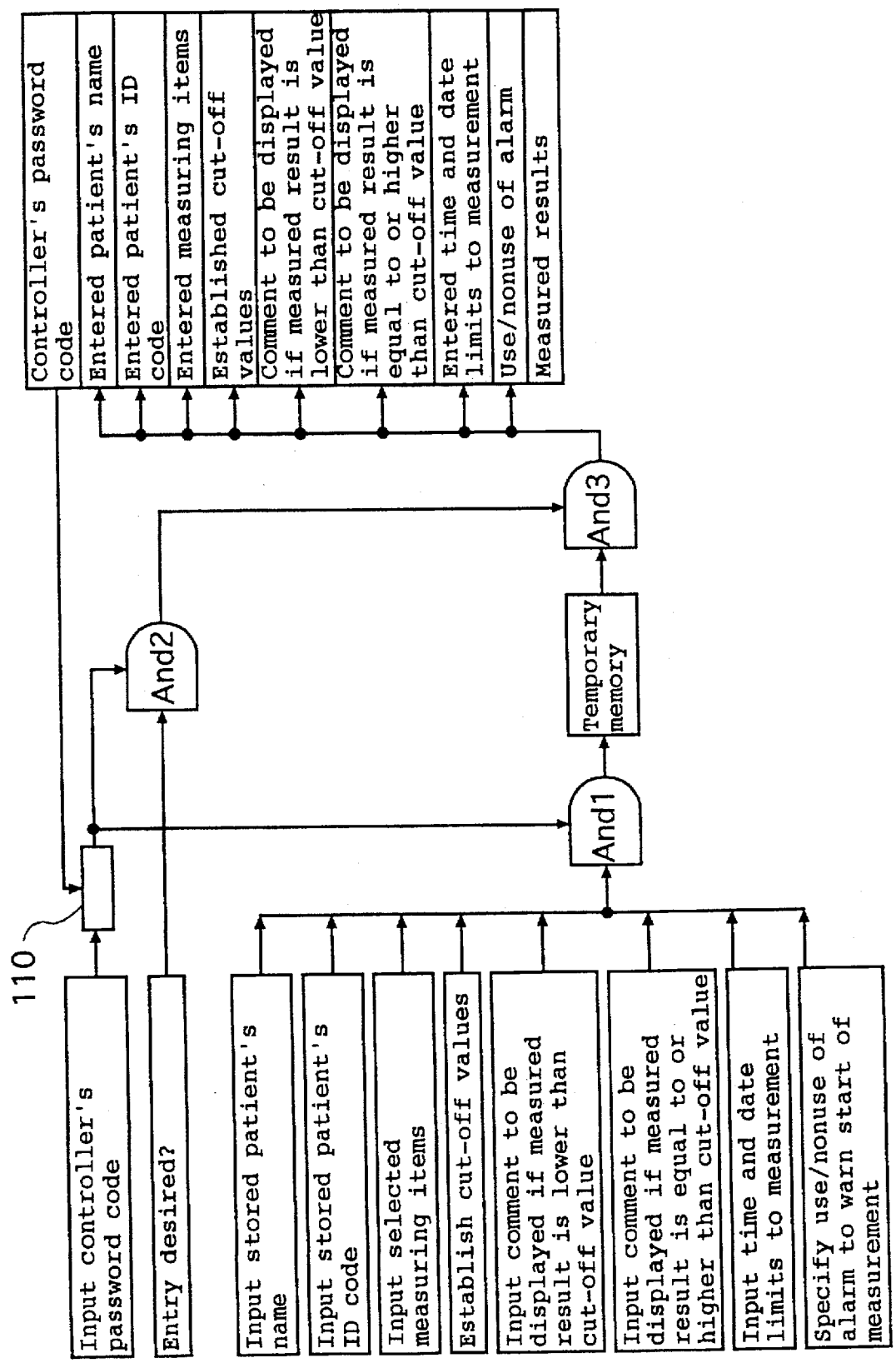
FIG. 18 is a conceptual view depicting how the controller operates the embodiment and how the control unit of the embodiment acts in response.

When the controller starts an entry procedure by activating a group of subject entry commands, the control unit 14 (or host computer) enters an operation mode shown in FIG. 18. The controller ID code entered through the keyboard is compared by a comparator 110 with the controller registration code stored in the storage means. In case of a match (a "true" output from the comparator), an AND gate 1 and an AND gate 2 are opened. The conditions entered and set from the keyboard 18 and from the push button switches and slide switches on the control panel are sent past the AND gate 1 for temporary storage into memory (RAM). When the "ENTER?" push button is clicked, the output of the AND gate 2 becomes "true" so as to open an AND gate 3. The settings in the temporary memory are then written to the applicable regions in the storage means.

Figure 19:
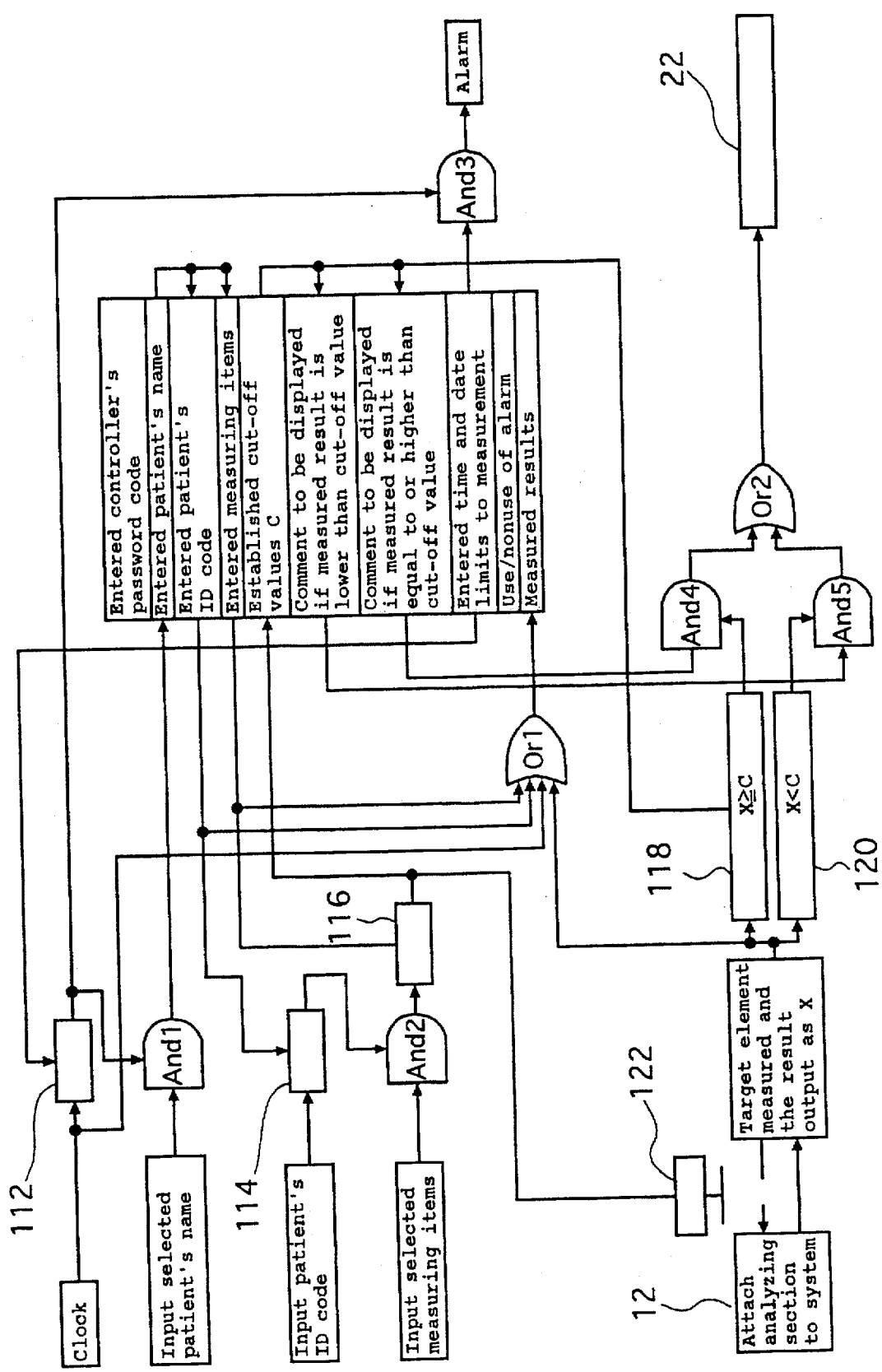
FIG. 19 is a conceptual view showing how the operator operates the embodiment and how the control unit of the embodiment acts in response.

Meanwhile, when the operator starts a group of measuring commands, the control unit or host computer enters a measurement mode shown in FIG. 19. In the measurement mode, the output of current time data from a built-in timer in the control unit 14 is compared by a comparator 112 with the settings of measurement date and time data stored in the storage device. If the output of the current time data from the timer falls on the allowed date and within the allowed time period, the comparator 112 outputs a "True" signal to open the AND gate 1 and an AND gate 3. Where the controller set alarm activation beforehand in the storage device, the opening of the AND gate 3 turns on a buzzer or other appropriate type of alarm. When the subject name is selected by use of a ring switch on the control panel of the control unit 14, the opening of the AND gate 1 is accompanied by the retrieval from the storage device of the patient's name, the patient's ID code and the relevant measuring items in accordance with the ring switch for the selected subject's name. The patient's ID code thus called up is compared by a comparator 114 with the subject's ID code entered from the keyboard. If the two codes coincide with each other (a "true" output from the comparator), the AND gate 2 is opened. With the AND gate 2 opened, the measuring item selected by a ring switch and the previously recalled measuring item are compared by a comparator 116. If the comparator 116 effects a "true" output, the output enables a switch that causes the installed measuring unit 12 to start measurement. This in turn triggers the retrieval from the storage device of the criterion (cut-off value) C and the comment in effect when the measured result taken is lower than, equal to, or more than the cut-off value in accordance with the ring switch for the selected target analyte to be analyzed.

Although not shown in FIG. 19, past measured results are retrieved if the comparator 116 effects the "True" output. The output of the comparator 116 opens the AND gate through which the past data is displayed on the control panel.

When the operator installs the measuring unit 12, introduces a specimen into the measuring unit 12 (i.e., analyzing section 12a), and turns on the measurement start switch (indicated by numeral 122 in FIG. 19). This causes the measuring unit 12 to start measurement. The measured result of the target analyte is computed from the electrical signals supplied by the measuring unit 12. The value X is compared with the cut-off value C by comparators 118 and 120. Depending on whether $X \geq C$ or $X < C$, either an AND gate 4 or an AND gate 5 is opened. Then the relevant comment set by the controller is sent through an OR gate 2 for display onto the control panel. The measured result of the target analyte for analysis is stored into the storage device past an OR gate 1 along with such data as the patient's ID code, the measuring items and the measurable time.

In the examples discussed above, not all items need to be stored into a single storage device. The items may be stored in a distributed manner in a plurality of storage devices. Alternatively, the same data may be stored in duplicate fashion in a plurality of storage devices. The alternative way of storing the same data in a plurality of storage devices is desirable from the standpoint of data security. The storage device(s) may or may not be attached fixedly to the control unit. The storage device(s) may be allocated in the host computer connected via communication lines, or may be of a type detachable from the control unit such as an IC card, as discussed earlier.

When the controller sets commands with respect to the measurements taken according to the criteria, such commands may be formed in files as command Groups and stored in the storage device. The command Groups, written in a language executable by the CPU of the control unit, may include programs written in machine language, in macro control commands such as assembler, or in higher level languages such as C, FORTRAN and BASIC. It may be desired that the CPU control devices built in or externally attached to the control unit. Such devices may comprise the measuring unit, storage unit, alarm, communication interface, modem, facsimile machine, data I/O interface and relay circuit. In those cases, the above-mentioned command Groups are supplemented by other groups of commands that are specific to the respective devices. For example, some devices are controlled by use of commands associated with the RS-232C port, parallel port or GPIB bus. Various commands may be used depending on the nature of what needs to be controlled and on the type of device to be controlled. Illustratively, there are commands that are used to modify the preliminary questions, measuring items, criteria for judgment, the comments and commands about the measured results according to the criteria, and the measurable date and time. These groups of commands are furnished initially to designate in the applicable storage unit the address of the settings desired to be modified so that they may be updated. For example, if a particular setting of the criteria exists at a specific logical address on the hard disc in the control unit, that logical address may be designated as a parameter 1, and commands for writing a parameter 2 (new setting) are preserved in the form of a preset command file. Although such command groups may be set originally by the controller, it is preferable to prepare beforehand a plurality of groups of frequently used commands as files inside the system so that the controller may simply designate the appropriate file name and parameters when setting up the commands. In the setup above, preparing commands for modifying a setting of the criteria requires three things: specifying a preset command file (comprising storage update commands), setting the parameter 1 to designate modification of the criteria, and setting the parameter 2 to designate the new setting of the criteria. As in the case of the comment display described earlier, a comparator compares the cut-off value C with the measured result X about the target analyte for analysis, the value X being computed from the electrical signals sent by the measuring unit. The corresponding command file to be set by the controller is retrieved from the storage means and executed. As described, the simplest and the least error-plagued method for the controller to set command groups is first to store all commands beforehand in the storage means, and then to select any of them in the form of a command file at the time of the controller's registration of the subject into the apparatus. In this case, selecting a plurality of files causes the command groups in the selected files to be executed, provided the measured results satisfy the criteria. The command execution means outlined above is only an example and may be replaced by any other means by which the control unit may execute commands.

While a preferred embodiment of the invention has been described using specific terms, such description is for illustrative purposes only, and it is to be understood that changes and variations may be made without departing from the spirit and scope of the claims that follow.

EXPLOITATION IN INDUSTRY

As described, the medical measurement apparatus according to the invention allows not only health-care professionals such as doctors but also test subjects such as patients and pregnant women as well as their attendants to readily perform medical measurement in medical institutions or elsewhere (e.g., at home). Furthermore, the inventive medical measurement apparatus permits health-care experts such as doctors with specialized knowledge to set appropriate comments about a given subject with respect to relevant measuring items, the criteria for judgment and the measured results. The judgments as per the criteria regarding the measured results and the relevant comments corresponding to such judgments are output suitably by the apparatus.

With this medical measurement apparatus in use, the subject staying at home can receive specialized medical care, reassured knowing that he or she is under specialists' supervision. In addition, the use of the measurements taken by this apparatus significantly helps doctors and other medical care experts in providing appropriate medical care to their patients.

What is claimed is:

1. A medical measurement apparatus, wherein an amount of a target analyte in a sample of a subject is measured, said apparatus comprising:

a measuring unit for outputting electrical signals in accordance with the amount of the target analyte; and a control unit including, identification means for identifying the subject by receiving specific identification data corresponding to the subject and for verifying the specific identification data;

measurement criteria-setting means for setting measurement criteria corresponding to the target analyte and for setting comments corresponding to results of the target analyte wherein said measurement criteria-setting means is only used by a controller, capable of making a specialized judgment on the amount of the target analyte in the sample; and judgment and display means for computing measurements based on the electrical signals from said measuring unit, for selecting appropriate comments corresponding to the measurements using the measurement criteria, and for displaying the appropriate comments;

wherein said control unit includes storage means for storing a plurality of measurements, wherein said control unit, the plurality of measurements are retrieved by the controller;

wherein said control unit, the measurement criteria is modified in accordance with the plurality of measurements.

2. A medical measurement apparatus, wherein an amount of a target analyte in a sample of a subject is measured, said apparatus comprising:

a measuring unit for outputting electrical signals in accordance with the amount of the target analyte; and a control unit including, identification means for identifying the subject by receiving specific identification data corresponding to the subject and for verifying the specific identification data;

measurement criteria-setting means for setting measurement criteria corresponding to the target analyte and for setting comments corresponding to results of the target analyte wherein said measurement criteria-setting means is only used by a controller, capable of making a specialized judgment on the amount of the target analyte in the sample; and judgment and display means for computing measurements based on the electrical signals from said measuring unit, for selecting appropriate comments corresponding to the measurements using the measurement criteria, and for displaying the appropriate comments;

wherein said control unit includes a time stamper;

means for setting measurement time-related criteria corresponding to the target analyte; and measurement time-verifying means for verifying whether the measurement has been correctly carried out in accordance with the measurement time-related criteria;

wherein said control unit is configured so that only the controlled can set the measurement time-related criteria.

3. A medical measurement apparatus, wherein an amount of a target analyte in a sample of a subject is measured, said apparatus comprising:

a measuring unit for outputting electrical signals accordance with the amount of the target analyte; and a control unit including, identification means for identifying the subject by receiving specific identification data corresponding to the subject and for verifying the specific identification data;

measurement criteria-setting means for setting measurement criteria corresponding to the target analyte and for setting comments corresponding to results of the target analyte wherein said measurement criteria-setting means is only used by a controller, capable of making a specialized judgment on the amount of the target analyte in the sample; and judgment and display means for computing measurements based on the electrical signals from said measuring unit, for selecting appropriate comments corresponding to the measurements using the measurement criteria, and for displaying the appropriate comments;

wherein when said identifying means cannot verify the specific identification data, said apparatus will not permit the measurement to be carried out or will give an alarm.

4. A medical measurement apparatus, wherein an amount of a target analyte in a sample of a subject is measured, said apparatus comprising:

a measuring unit for outputting electrical signals in accordance with the amount of the target analyte; and a control unit including, identification means for identifying the subject by receiving specific identification data corresponding to the subject and for verifying the specific identification data;

measurement criteria-setting means for setting measurement criteria corresponding to the target analyte and for setting comments corresponding to results of the target analyte wherein said measurement criteria-setting means is only used by a controller, capable of making a specialized judgment on the amount of the target analyte in the sample; and judgment and display means for computing measurements based on the electrical signals from said measuring unit, for selecting appropriate comments corresponding to the measurements using the measurement criteria, and for displaying the appropriate comments;

wherein said measurement criteria-setting means selects the target analyte to be measured depending on the subject.

5. A medical measurement apparatus, wherein an amount of a target analyte in a sample of a subject is measured, said apparatus comprising:

a measuring unit for outputting electrical signals in accordance with the amount of the target analyte; and a control unit including, identification means for identifying the subject by receiving specific identification data corresponding to the subject and for verifying the specific identification data;

measurement criteria-setting means for setting measurement criteria corresponding to the target analyte and for setting comments corresponding to results of the target analyte wherein said measurement criteria-setting means is only used by a controller, capable of making a specialized judgment on the amount of the target analyte in the sample; and judgment and display means for computing measurements based on the electrical signals from said measuring unit, for selecting appropriate comments corresponding to the measurements using the measurement criteria, and for displaying the appropriate comments;

wherein said control unit further includes questioning means for asking the subject a set of questions corresponding to the target analyte to be detected before carrying out a measurement, wherein said control unit is configured so that only the controller can operate said questioning means to ask the set of questions;

wherein said control unit further includes verification means for determining whether the measurement has been carried out in accordance with measurement conditions preliminarily set corresponding to the target analyte to be detected, wherein said control unit is configured so that only the controller can operate said verification means to set the measurement conditions.

6. A medical measurement apparatus, wherein an amount of a target analyte in a sample of a subject is measured, said apparatus comprising:

a measuring unit for outputting electrical signals in accordance with the amount of the target analyte; and a control unit including, identification means for identifying the subject by receiving specific identification data corresponding to the subject and for verifying the specific identification data;

measurement criteria-setting means for setting measurement criteria corresponding to the target analyte and for setting comments corresponding to results of the target analyte wherein said measurement criteria-setting means is only used by a controller, capable of making a specialized judgment on the amount of the target analyte in the sample; and judgment and display means for computing measurements based on the electrical signals from said measuring unit, for selecting appropriate comments corresponding to the measurements using the measurement criteria, and for displaying the appropriate comments;

wherein said control unit further includes verification means for determining whether a measurement has been carried out in accordance with measurement conditions preliminarily set corresponding to the target analyte to be detected, wherein said control unit is configured so that only the controller can operate said verification means to set the measurement conditions.

* * * * *

UNITED STATES PATENT AND TRADEMARK OFFICE
CERTIFICATE OF CORRECTION

PATENT NO. : 5,730,124
DATED : March 24, 1998
INVENTOR(S) : Tadakazu YAMAUCHI

It is certified that error appears in the above-indentified patent and that said Letters Patent is hereby corrected as shown below:

On title page, item [75] change the inventor's address from "Saitama, Japan" to --Tokyo, Japan--.

Signed and Sealed this

Sixteenth Day of June, 1998

*Attest:*

BRUCE LEHMAN

*Attesting Officer*     Commissioner of Patents and Trademarks